(12) United States Patent
Johnson

(10) Patent No.: US 11,622,870 B1
(45) Date of Patent: *Apr. 11, 2023

(54) PROSTHETIC LIMB KIT AND METHOD OF MANUFACTURE

(71) Applicant: Phillip W. Johnson, Narrows, VA (US)

(72) Inventor: Phillip W. Johnson, Narrows, VA (US)

( * ) Notice: Subject to any disclaimer, the term of this patent is extended or adjusted under 35 U.S.C. 154(b) by 272 days.

This patent is subject to a terminal disclaimer.

(21) Appl. No.: 16/538,751

(22) Filed: Aug. 12, 2019

Related U.S. Application Data

(63) Continuation-in-part of application No. 15/613,045, filed on Jun. 2, 2017, now Pat. No. 10,376,390.

(60) Provisional application No. 62/344,954, filed on Jun. 2, 2016.

(51) Int. Cl.
| | | |
|---|---|---|
| *A61F 2/76* | (2006.01) | |
| *A61F 2/80* | (2006.01) | |
| *A61F 2/66* | (2006.01) | |
| *A61F 2/78* | (2006.01) | |
| *A61F 2/60* | (2006.01) | |
| *A61F 2/64* | (2006.01) | |
| *A61F 2/50* | (2006.01) | |

(52) U.S. Cl.
CPC ................. *A61F 2/76* (2013.01); *A61F 2/64* (2013.01); *A61F 2/66* (2013.01); *A61F 2/80* (2013.01); *A61F 2002/5083* (2013.01); *A61F 2002/607* (2013.01); *A61F 2002/6614* (2013.01); *A61F 2002/7806* (2013.01); *A61F 2002/7818* (2013.01); *A61F 2002/7837* (2013.01)

(58) Field of Classification Search
CPC ...... A61F 2/5044; A61F 2/5046; A61F 2/604; A61F 2/76; A61F 2002/5052; A61F 2002/5053; A61F 2002/5055; A61F 2002/7605; A61F 2002/761; A61F 2/50; A61F 2/60; A61F 2/601; A61F 2002/502; A61F 2002/5083; A61F 2002/5084
See application file for complete search history.

(56) References Cited

U.S. PATENT DOCUMENTS

| | | | |
|---|---|---|---|
| 41,934 A | 3/1864 | Monroe | |
| 1,153,532 A | 9/1915 | Apgar | |
| 2,696,011 A | 12/1954 | Galdik | |
| 3,461,464 A | 8/1969 | Lindgren | |
| 4,312,080 A | 1/1982 | Staats | |
| 4,459,709 A * | 7/1984 | Leal | A61F 2/601 156/60 |
| 4,872,879 A * | 10/1989 | Shamp | A61F 2/80 623/36 |

(Continued)

OTHER PUBLICATIONS

D-Rev, ReMotion Knee, http://d-rev.org/projects/mobility/, retrieved Jun. 2, 2017 (4 pages).

(Continued)

*Primary Examiner* — Christie L Bahena
(74) *Attorney, Agent, or Firm* — Allan A. Fanucci

(57) ABSTRACT

A prosthetic limb is made from a portable kit that is of relatively low cost and easy to assemble and custom fit to a person in need so that the person can wear the prosthetic immediately, without having to wait for the prosthetic to be manufactured off-site. The embodiments include a below the knee device and an above the knee device that includes an artificial knee. The improved prosthetic is suited for replacing a missing leg but can also be adapted to replace another body part such as an arm, hand or foot.

18 Claims, 19 Drawing Sheets

(56) References Cited

U.S. PATENT DOCUMENTS

| | | | |
|---|---|---|---|
| 4,911,709 | A | 3/1990 | Marlow et al. |
| 5,133,777 | A | 7/1992 | Arbogast et al. |
| 5,228,164 | A | 7/1993 | Graf et al. |
| 5,724,714 | A | 3/1998 | Love |
| 5,888,231 | A | 3/1999 | Sandvig et al. |
| 6,508,842 | B1 | 1/2003 | Caspers |
| 6,793,682 | B1 | 9/2004 | Mantelmacher |
| 7,883,547 | B2 | 2/2011 | Mantelmacher |
| 2004/0153168 | A1 | 8/2004 | Childress et al. |
| 2006/0173554 | A1* | 8/2006 | Slemker .................. A61F 2/64 623/38 |
| 2007/0055383 | A1 | 3/2007 | King |
| 2010/0114331 | A1 | 5/2010 | Mantelmacher |
| 2010/0304205 | A1 | 12/2010 | Jo et al. |
| 2014/0277584 | A1 | 9/2014 | Hurley et al. |

OTHER PUBLICATIONS

Travis Williams, "Nonprofit Hope to Walk helping injured get back on their feet," The Roanoke Times, Mar. 26, 2016 (9 pages); http://www.roanoke.com/news/local/blacksburg/nonprofit-hope-to-walk-helping-injured-get-back-on-their/article_1ae3a731-e6bf-5bb6-aa9e-09d2273d7bc2.html.

Kristi OConnor, "Johnson City man creates affordable prosthetics," News 5 WCYB, Sep. 30, 2015 (6 pages); http://www.wcyb.com/health/johnson-city-man-creates-affordable-prosthetics/14352346.

Össur Academy, "Össur Presents: Modular Socket System," Aug. 22, 2011 (1 page); https://www.youtube.com/watch?v=qx56HY5ephw; cited in Non-Final Office Action dated Jun. 28, 2018 and Final Office Action dated Nov. 1, 2018 for U.S. Appl. No. 15/613,045.

SPS (Closed End PVA Bags) [cited in Non-Final Office Action dated Jun. 28, 2018 and Final Office Action dated Nov. 1, 2018 for U.S. Appl. No. 15/613,045].

Techform (Fiberglass Casting Tape MDS) [cited in Non-Final Office Action dated Jun. 28, 2018 and Final Office Action dated Nov. 1, 2018 for U.S. Appl. No. 15/613,045].

Ossur (Modular Socket System—Direct Lamination [cited in Non-Final Office Action dated Jun. 28, 2018 and Final Office Action dated Nov. 1, 2018 for U.S. Appl. No. 15/613,045].

Non-Final Office Action issued for U.S. Appl. No. 15/613,045 dated Jun. 28, 2018 (14 pages).

Final Office Action issued for U.S. Appl. No. 15/613,045 dated Nov. 1, 2018 (17 pages).

* cited by examiner

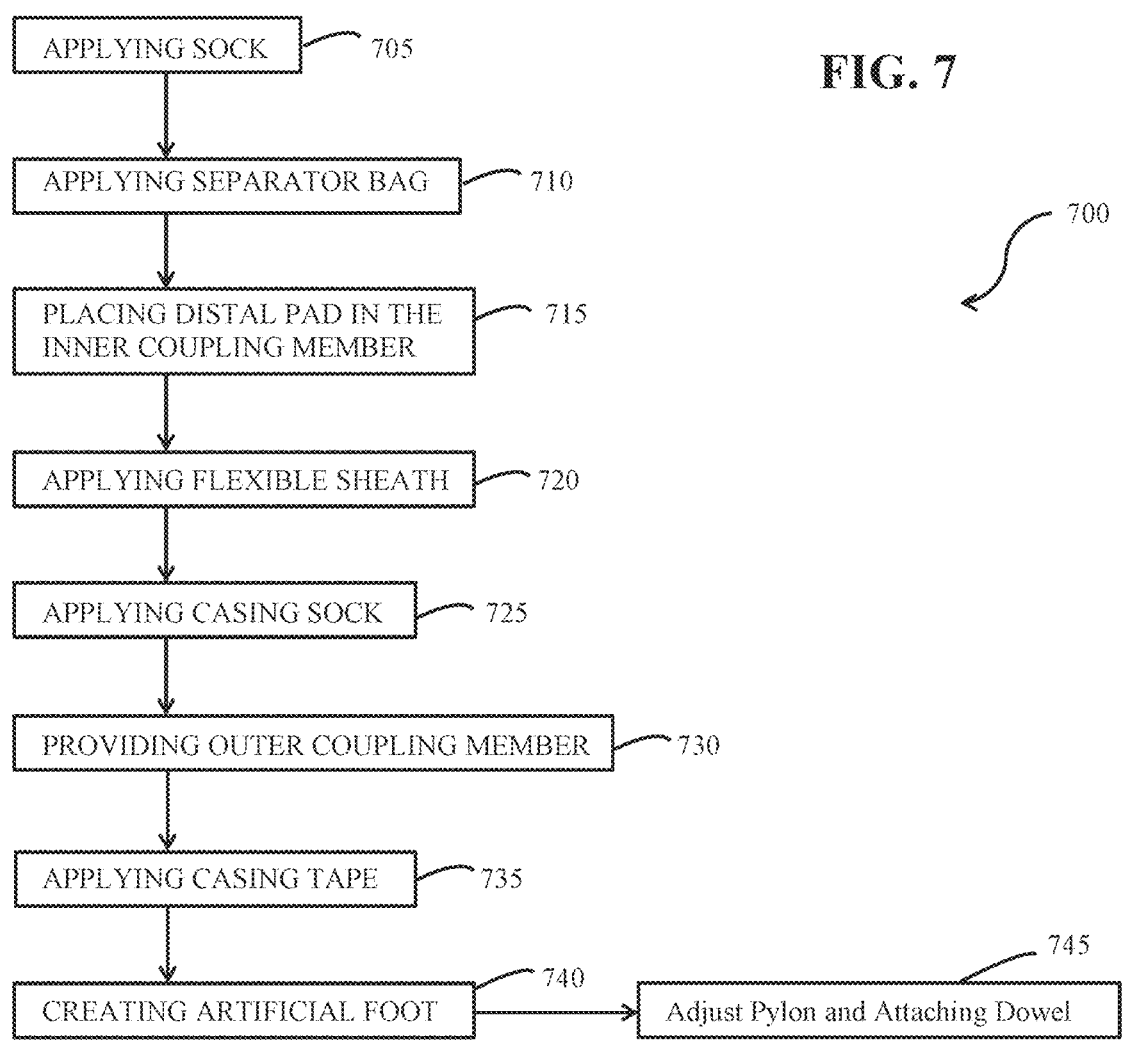

PROSTHETIC LIMB KIT AND METHOD OF MANUFACTURE

CROSS-REFERENCE TO RELATED APPLICATIONS

This application is a continuation-in-part of U.S. patent application Ser. No. 15/613,045, now U.S. Pat. No. 10,376,390, filed Jun. 2, 2017, which claims the benefit of U.S. Provisional Patent Application No. 62/344,954, filed Jun. 2, 2016. Each of the foregoing applications is expressly incorporated by reference herein.

FIELD OF THE INVENTION

The field of the invention relates to a prosthetic limb and method of making the prosthetic limb. In particular, the invention provides a portable kit that is of relatively low cost and easy to assemble and custom fit to a person in need so that the person can wear the prosthetic immediately, without having to wait for the prosthetic to be manufactured off-site.

DESCRIPTION OF THE RELATED ART

Throughout history, humans have lost limbs as a result of accidents, military combat, illnesses, and hereditary defects. In the United States, approximately 2 million people have had amputation of an arm or leg. As medical science improved, prosthetic limbs became available. Prosthetics are artificial devices that replace missing body parts.

Prosthetics have been manufactured out of metals, plastics, wood, leather, carbon fiber, polycarbonates, resins, and laminates. To achieve a customized and comfortable fit, health care providers typically saw an amputee, took measurements, and made a cast. The cast was then sent offsite to a manufacturing facility, where a socket would be created, often out of a synthetic material. The socket would be mailed to the prosthetic provider. At that point, the amputee would return to the prosthetic provider to be fit into the socket. However, during the long time between the initial making of the cast and the delivery of the socket, the amputee's limb stump has changed in shape, size and/or dimension through, for example, atrophy, weight loss, weight gain, or other reasons. If the socket did not fit the amputee well, the provider could make minor adjustments to the socket. But if the socket required a substantial change, a new cast has to be made and the time-consuming process of manufacturing a new socket would have to be repeated, after which there is no guarantee that the revised socket would fit yet again. Therefore, there is a need for a prosthetic that can be built to custom fit an amputee so the amputee can walk out on a working prosthetic without having to wait for the prosthetic to be manufactured off-site.

SUMMARY OF THE INVENTION

As an aspect of the novel kit and method described herein, an example embodiment is a prosthetic limb that is provided in a kit with easy to assemble features so that it can be created on a person in need quickly and efficiently. Thus, the person can be fitted with the prosthetic limb at their location, without having to forward measurements to a different location where the prosthetic would be manufactured. The improved prosthetic is suited for a missing body part such as an arm, leg, hand, or foot.

The present invention now provides a kit for preparing a prosthetic leg for a person having a missing portion of a leg and a remaining stump. The kit comprises a plurality of components including a sock adapted to fit over the person's stump; a separator bag adapted to cover the sock and the person's stump; a distal pad configured and dimensioned for placement below the person's stump to provide cushioning; an inner coupling member having a concave lower surface and an upper inner surface forming an opening configured and dimensioned to receive at least part of the distal pad therein and to hold the distal pad in position below the person's stump; a flexible sheath having a closed end adapted to receive the inner coupling member and distal pad therein and an open end which allows the sheath to be extended over the separator bag and sock to hold the inner coupling member and the distal pad against the person's stump; a casting sock comprising a fabric containing a water activated settable material that, after activation, is adapted to fit over the flexible sheath, the inner coupling member, the distal pad, and at least part of the separator bag and the sock when those components are in position on the person's stump; an outer coupling member having a lower surface that includes a socket having an opening, and an upper surface configured to receive the concave lower surface of the inner coupling member and being at least partially conformable about the inner coupling member; a casting tape comprising a fabric containing a water activated settable material and provided in a length or lengths that, after activation, are sufficient for attaching the outer coupling member to the person's stump while also covering the flexible sheath, the inner coupling member, the distal pad, and at least part of the separator bag and sock when those components are in position on the person's stump; a wooden dowel and a pylon comprising a plastic hollow tube configured to receive the wooden dowel, each of the wooden dowel and the pylon having a length that is adjustable to provide an overall length for the prosthetic leg to conform to the length needed for the person; components for forming an artificial foot comprising a plurality of shapeable members, one of which includes a hole for accommodating the pylon; and an adhesive for attaching the foot components together, for attaching the pylon or the wooden dowel to the hole of the foot component and to the socket opening of the outer coupling member, and for attaching the outer coupling member to the casting sock. In some embodiments, the kit may further comprise an artificial knee joint that is operatively associated with the pylon to provide knee movement to the prosthesis when constructed.

Another embodiment of the invention is a method for preparing a prosthetic leg from the kit for a person having a missing portion of a leg and a remaining stump, which comprises applying the sock over the person's stump; applying the separator bag over the sock and the person's stump; placing the distal pad below the person's stump; placing an inner coupling member below the distal pad to receive at least part of the distal pad therein and to hold the distal pad in position below the person's stump; applying the flexible sheath with the closed end placed around the inner coupling member and distal pad and with the open end extending the sheath over the separator bag and sock to hold those components against the person's stump; activating the casting sock by immersion in water and applying the activated casting sock to the flexible sheath; providing the upper surface of the outer coupling member beneath the closed end of the flexible sheath with the upper surface receiving the concave lower surface of the inner coupling member; conforming the upper surface of the outer coupling member at least partially about the distal pad; activating the casting tape by immersion in water; attaching the outer coupling member to the person's stump by wrapping the activated casting tape around the outer coupling member while also covering the flexible sheath, the inner coupling member, the distal pad, and at least part of the separator bag and sock when those components are in position on the person's stump; cutting the pylon to an appropriate length so that the prosthetic leg provides the correct height for the person; shaping the artificial foot components; adhesively attaching the shaped components of the artificial foot together to form the artificial foot; and adhesively attaching one end of the pylon to the socket opening of the outer coupling member and the other end of the pylon to the hole in the foot component of the artificial foot. When the kit further comprises an artificial knee, the pylon is cut with a saw or knife to receive the artificial knee and to position the knee at a correct anatomical location for the person.

In accordance with principles of the present, another kit for preparing a prosthetic leg for a person having a missing portion of a leg and a remaining stump is contemplated. The kit comprises a plurality of components which includes a flexible sheath adapted to fit on the person's stump. The flexible sheath is a warped plastic sheet with two opposite sides being curved toward each other, and is flexible to be opened from the two opposite sides to fit the flexible sheath on the person's stump and close on the person's stump. The components also includes a casting sock comprising a fabric containing a water activated settable material that, after activation, is adapted to fit over the flexible sheath. The components further includes a coupling member having a lower surface that includes an opening, and an upper surface configured to receive the person's stump covered by the casting sock. Additionally, the components include a casting tape comprising a fabric containing a water activated settable material and provided in a length or lengths that, after activation, are sufficient for attaching the coupling member to the person's stump while also covering the flexible sheath. Moreover, the components include a pylon comprising a plastic hollow tube configured to engage the coupling member. The pylon has a length that is adjustable to provide an overall length for the prosthetic leg to conform to the length needed for the person. Furthermore, the components include an artificial foot comprising a hole for accommodating the pylon.

In one embodiment, the flexible sheath includes a gap between the two opposite sides. The gap is between 0.1 inch and 1 inch.

In one embodiment, the flexible sheath has a length to expose a front end of the person's stump.

In one embodiment, the flexible sheath includes a concave region on a top side of the flexible sheath to accommodate an inner area of the person's stump. The concave region or area surrounding the concave region is configured to have its edge extending away from the warped plastic sheet.

In one embodiment, the two opposite sides of the flexible sheath contact or overlap each other.

In another embodiment, the kit further comprises a flexible panel to fit on an arc of the person's stump. The flexible panel has a width shorter than that of the plastic sheet.

In another embodiment, the kit further comprises an artificial knee joint that is operatively associated with the pylon to provide knee movement to the prosthesis when constructed. The kit further comprises a second pylon and the second pylon is shorter than the pylon and is configured to connect the artificial knee and the coupling member.

In another embodiment, the kit further comprises adhesive or screws for attaching the pylon to the hole of the artificial foot and to the opening of the coupling member.

in one embodiment, the casting tape comprises fabric or fiberglass and the settable material comprises polyurethane resin.

in accordance with principles of the present invention, another method for preparing a prosthetic leg from the above kit for a person having a missing portion of a leg and a remaining stump is contemplated. The method comprises applying the flexible sheath on the person's stump. The flexible sheath is applied by opening the flexible sheath by pushing the two opposite sides away from each other, placing the opened flexible sheath on the person's stump, and closing the flexible sheath by directing the two opposite sides toward each other. The method also comprises activating the casting sock by immersion in water and applying the activated casting sock to the flexible sheath. The method further comprises providing the coupling member beneath the casting sock with the upper surface of the coupling member contacting the casting sock. Additionally, the method comprises activating the casting tape by immersion in water and attaching the coupling member to the person's stump covered by the casting sock by wrapping the activated casting tape around the coupling member while also covering the flexible sheath. Moreover, the method comprises cutting the pylon to an appropriate length so that the prosthetic leg provides the correct height for the person. Furthermore, the method comprises providing the artificial foot and attaching one end of the pylon to the opening on the lower surface of the coupling member and the other end of the pylon to the hole in the artificial foot.

in one embodiment, the flexible sheath is applied on the person's stump to expose a front end of the person's stump. The activated casting sock is applied to the flexible sheath from the exposed front end of the person's stump.

In one embodiment, the kit further comprises a flexible panel to fit on an arc of the person's stump and the flexible panel is applied to cover area not covered by the flexile sheath.

In one embodiment, the kit further comprises an artificial knee and the pylon is cut with a saw or knife to receive the artificial knee and to position the artificial knee at a correct anatomical location for the person. The kit further comprises a second pylon and the second pylon is installed to connect the acritical knee and the coupling member.

In one embodiment, the casting tape is applied in a manner to ensure that no air bubbles or voids are present between the casting tape and the coupling member and between the casting tape and the casting sock.

Other kits, methods, features and advantages of the invention will be or will become apparent to one with skill in the art upon examination of the following figures and detailed description. It is intended that all such additional systems, methods, features and advantages be included within this description, be within the scope of the invention.

BRIEF DESCRIPTION OF THE DRAWINGS

Preferred features of the invention are now provided by the appended drawings figures, wherein:

FIG. 7 depicts an illustrative flow chart for the method of preparing a prosthetic leg from the prosthetic kit in accordance with sonic embodiments of the present invention.

Figure 1:
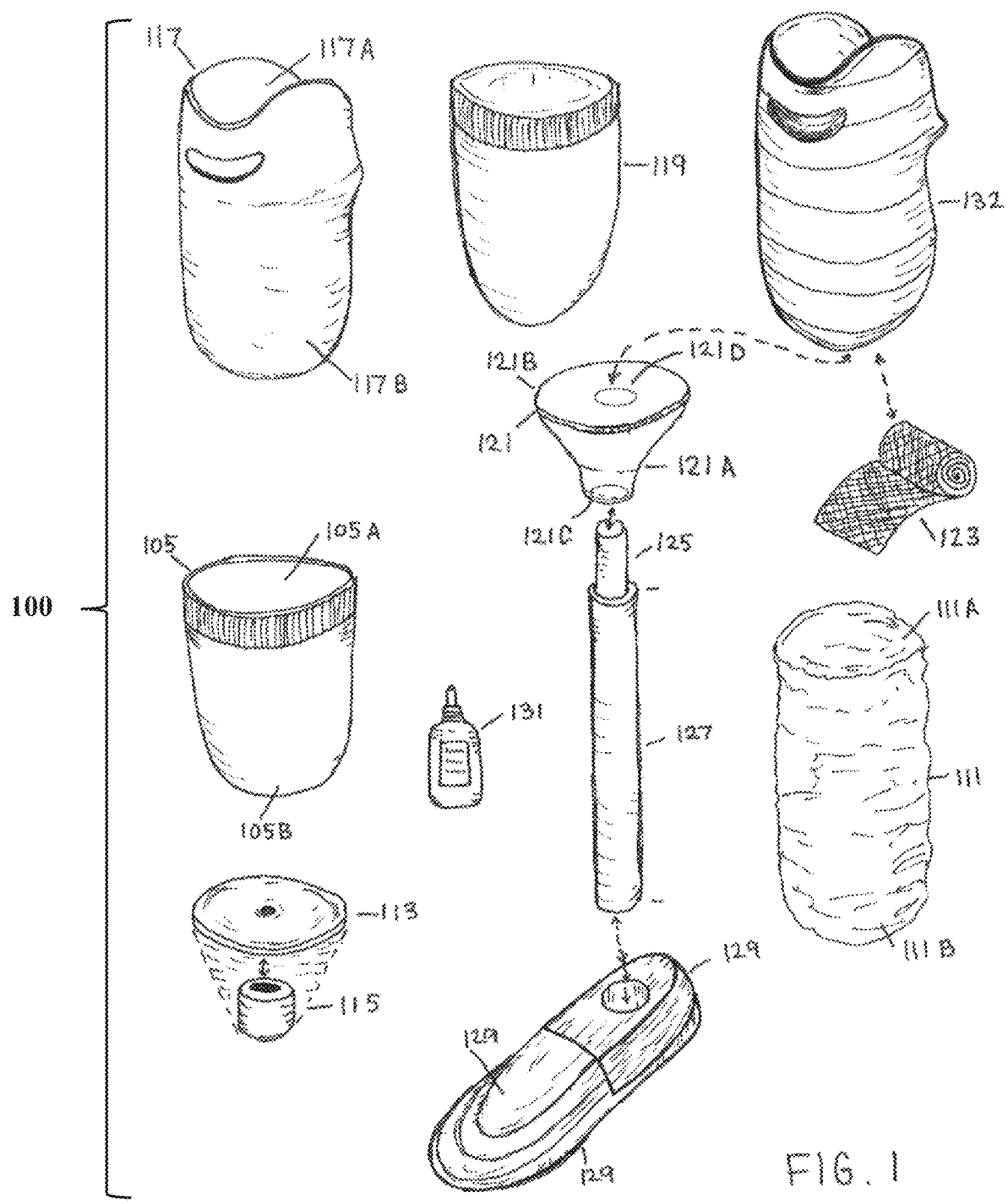
FIG. 1 depicts the components of a prosthetic leg kit according to the present invention.

The components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes is illustrated schematically rather than literally or precisely.

DETAILED DESCRIPTION OF THE INVENTION

The disclosed embodiments are for a kit for preparing a prosthetic limb and a method of making the prosthetic limb using the kit. The prosthetic limb can be made directly on a person in need, and by enabling a same day fit, the prosthetic limb contributes to improving the lifestyle of the person in need much sooner than by conventional manufacture, at a much lower cost. The size of the kit makes it transportable and thus serves the needs of amputees who are located in remote geographies or potentially even at the site of the amputation, such as in a war zone. In addition, the prosthetic can be created inexpensively. The invention is not limited to the below-described embodiments, but the invention can cover appropriate changes to the embodiments.

Turning now to the drawings, FIG. 1 depicts an illustrative prosthetic kit 100, which in this particularly preferred embodiment, is a kit for preparing a prosthetic leg. The kit 100 is designed for a person having a missing portion of a leg and a remaining stump. The kit 100 may comprise a plurality of components, including a sock 105, a separator bag 111, a distal pad 113, an inner coupler 115, a flexible sheath 117, a casting sock, 119, an outer coupler 121, a casting tape 123, a dowel 125, a pylon 127, components for forming an artificial foot 129, and an adhesive 131. Each of the plurality of components is low-cost and is made from low-cost materials and/or manufactured at low-cost. Low-cost may refer to materials able to be purchased inexpensively from generally available materials that can be tailored or conformed to the person in need using readily available and simple manufacturing tools or machines. Thus, the kit allows the preparation of the prosthetic leg at relatively low cost in just about any location. It also is particularly useful for persons in low income or poverty areas. The prosthetic leg prepared from the kit 100 is substantially less expensive compared to prostheses currently in the market which may cost between $5,000 and $50,000. The kit 100 generally costs less than $50, and the prosthetic leg prepared from the kit 100 by a health care professional would cost than less $200. Therefore, the prosthetic leg prepared from the kit 100 costs less than 1% to 5% of an average-cost prosthesis in the current market. The prosthetic leg is also simple to create such that it is built by a layperson, e.g., a family member or a friend, after reading the preparation steps and instruction details provided in the kit as described herein. The kits can also be provided at no cost by being donated to certain impoverished or war torn areas. In those situations, the prosthetic leg would be provided at an even lower cost or even at no cost to person that would otherwise not be able to obtain one.

For preparing the prosthetic leg, the sock 105 is first placed on the person's stump. The sock 105 directly touches the person's stump and provides some buffer between the skin and the remaining components, just like a sock worn on a foot provides cushioning to shoes which are worn on the foot. The sock 105 is typically a fabric sock that may made of cotton, wool, nylon, acrylic, polyester, olefins (such as polypropylene), spandex, linen, or any combination thereof. The fabric sock may also be made of other materials that provide comfort to the person's stump. The sock 105 has an open end 105*a* and a closed end 105*b*, and the open end 105*a* and the closed end 105*b* are typically the opposite ends of the sock 105.

The separator bag 111 is adapted to cover the sock 105 and the person's stump to provide a flexible barrier to the additional components that are to be added. The sock 105 receives the separator bag 111 from the closed end 105*b*. The separator bag 111 has a size or volume sufficient to cover the area on the sock 105 where the subsequently applied casting sock 119 and casting tape 122 will be applied. The separator bag 111 has an open end 111*a* and a closed end 111*b*, and a longitudinal length (from the open end 111*a* to the closed end 111*b*) that is longer than that of the casting tape 119. The separator bag 111 is put on the sock 105 from the closed end 105*b* toward the open end 105*a* through the open end 111*a*. The open end 111*a* has a diameter that is larger than that of the tip 105*b*. The open end 111*a* and the closed end 111*b* are two opposite ends of the separator bag 111. The separator hag 111 is preferably made of a waterproof material, such as polyurethane, polyamide, polyester, polyolefin (e.g., polyethylene and polypropylene), fluoropolymer, or any combination thereof. Other materials and combinations having similar characteristics may also be used. The separator bag 111 prevents the settable material of the casting sock 119 and/or the casting tape 123 and water from soaking the sock 105 or contacting the person's stump. The separator bag 111, for example, is conveniently a plastic tubular bag.

The distal pad 113 is configured and dimensioned for placement below the person's stump to provide cushioning. The distal pad 113 is configured to have a shape and/or structure that conforms or matches the shape of the person's stump. The distal pad 113 is dimensioned to have a size that fits below the person's stump and is typically a foam or gel material of a polyurethane, polyethylene, polyester, polyvinylchloride (PVC), silicone, rubber, or any combination thereof. Other materials and combinations having similar characteristics may also be used. The distal pad 113 is made to be softer or more resilient compared to the inner coupling member 115 to absorb shock and vibration and to provide comfort.

Figure 2:
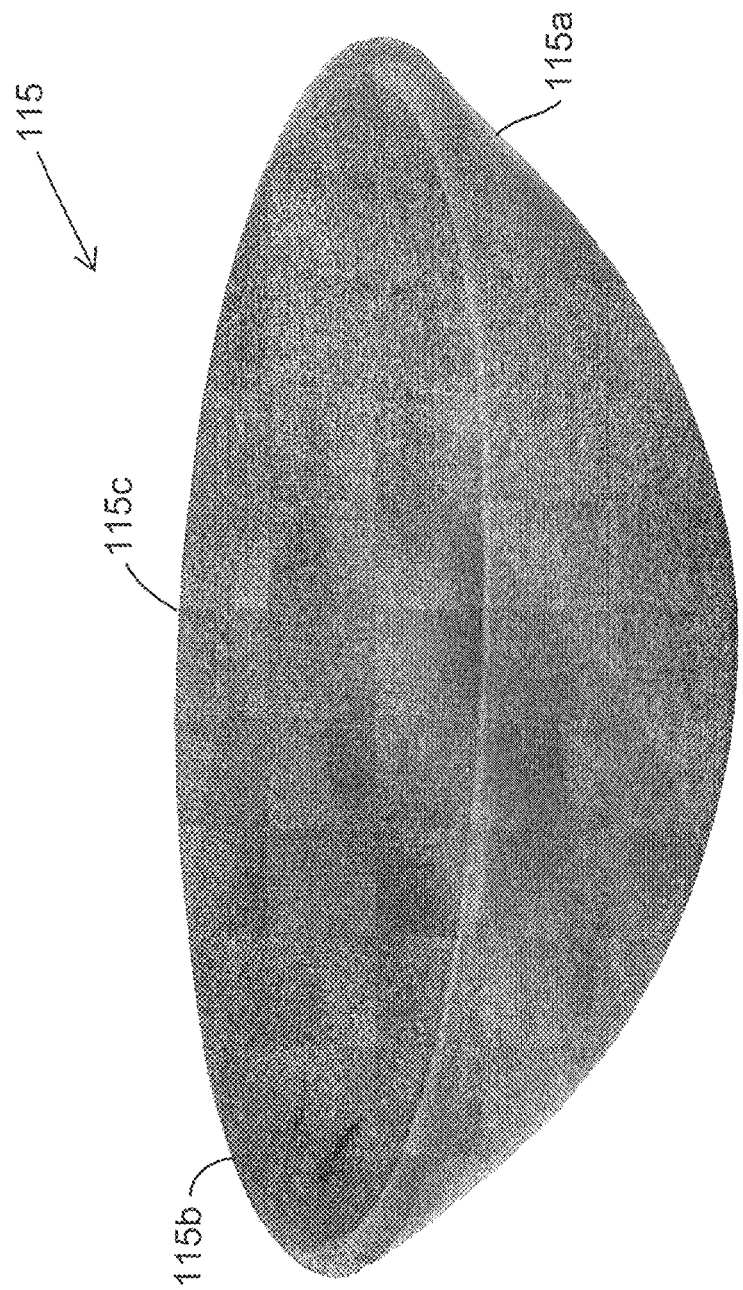
FIG. 2 depicts an illustrative inner coupling member in accordance with some embodiments with of the present invention.

FIG. 2 depicts an illustrative inner coupling member 115. The inner coupling member 115 has a concave lower surface 115a and an upper inner surface 115b. The upper inner surface 115b may form an opening 115c configured and dimensioned to receive at least part of the distal pad 113 and to hold the distal pad 113 in position below the person's stump. The opening 115c is configured to have a shape and/or structure that conforms or matches the shape and/or structure of the distal pad 113. The opening 115c is dimensioned to have a diameter or a depth that a portion of the distal pad 113 or the entire distal pad 113 is placed within the opening 115c. The inner coupling member 115 is preferably made of a plastic material such as polyvinyl chloride (PVC) or polypropylene, but it may also be made of the same material as the distal pad 113 or as the outer coupling member 121. Typically, however, the inner coupling member 115 is harder or less resilient compared to the distal pad 113 to provide protection to the distal pad 113 and the person's stump.

Figure 3:
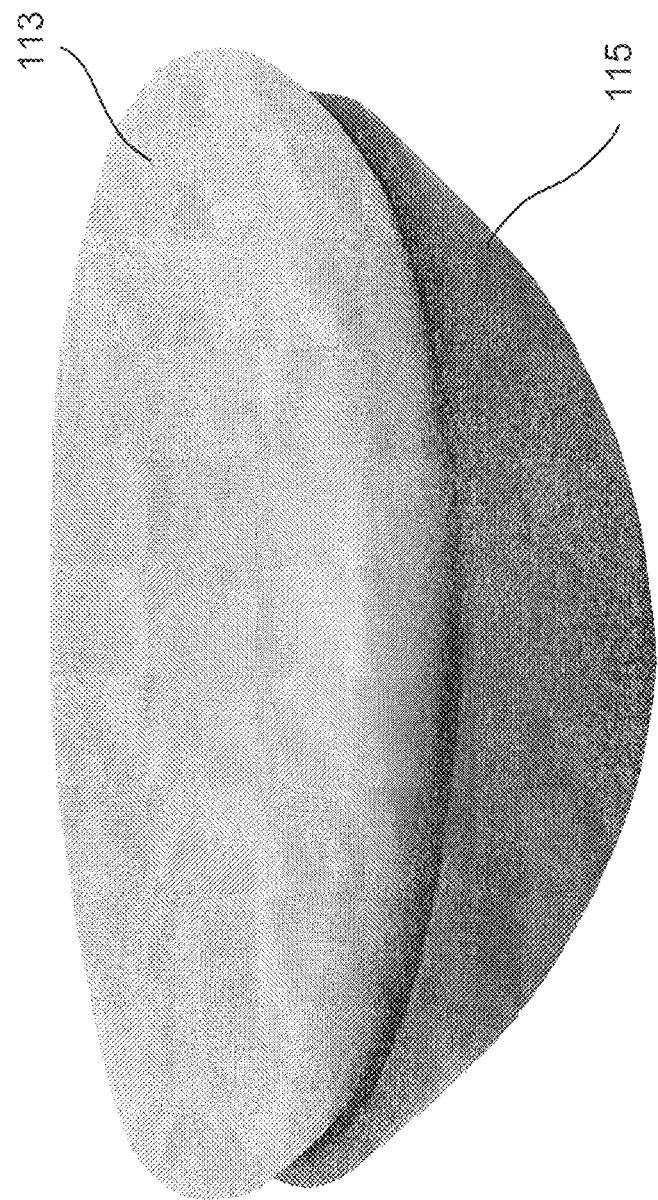
FIG. 3 depicts an illustrative inner coupling member receiving an illustrative distal pad in accordance with some embodiments of the present invention.

FIG. 3 depicts the inner coupling member 115 receiving the distal pad 113. The distal pad 113 may similarly have a concave lower surface and an upper inner surface, and the inner coupling member 115 may receive the distal pad 113 in a direction such that the concave lower surface of the distal pad 113 enters the opening 115c of the inner coupling member 115 first and contacts the upper inner surface 111b of the inner coupling member 115. The distal pad 113 may be larger or smaller than the inner coupling member 115 but generally they are essentially the same size.

Referring back to FIG. 1, the flexible sheath 117 is adapted to hold the inner coupling member 115 and the distal pad 113 against the person's stump. The flexible sheath 117 has an open end 117a adapted to receive the inner coupling member 115 and the distal pad 113 and a closed end 117b adapted to hold the inner coupling member 115 and the distal pad 113. The open end 117a may also allow the flexible sheath 117 to be extended over the separator bag and the sock 105 (hence the word "flexible") to hold the inner coupling member 115 and the distal pad 113 against the person's stump. The open end 117a may receive the inner coupling member 115 and the distal pad 113 with the inner coupling member 115 entering first. In particular, it is the concave lower surface 115a of the inner coupling member 115 that enters first. The closed end 117b may hold the inner coupling member 115 and the distal pad 113 with the inner coupling member 115 contacting the closed end 117b. In particular, it is the concave lower surface 115a of the inner coupling member 115 that contacts the closed end 117b. The flexible sheath 117 may be made of the same material as the sock 105 or of a different material. The flexible sheath 117 is preferably made of rubber or an elastomeric material or of another material that has similar flexibility characteristics. The flexible sheath 117 is made to elastically hold the separator bag 111 with the inner coupling member 115 and distal pad 113 therein tightly upon the sock 115. Tighter may refer to being harder to be removed from a person's stump or foot compared to the sock 105. Tightly refers to the situation that the person wearing the flexible sheath 117 feels that the flexible sheath 117 exerts more pressure on the person's stump or foot compared to the sock 105. The flexible sheath 117, for example, is a flexible synthetic stocking or expandable tube.

The casting sock 119 may comprise a fabric containing a water activated settable material. The fabric is made of the same material as the sock 105 or a different fabric material that is sufficiently porous to hold the settable material. The casting sock 119 is preferably made of polyester. The water activated settable material may comprise resin such as polyurethane resin, polyester resin, polyisocyanate resin, epoxy resin, plaster, or the like. The water activated settable material is preferably polyurethane resin. The casting sock 119 is activated by providing water to it. In one embodiment, the casting sock 119 is simply immersed in water for activation. Once activated, the casting sock 119 is applied to fit over the inner coupling member 115, the distal pad 113, and at least part of the flexible sheath 117, the separator bag 111, and the sock 105 when those components are in position with the person's stump. When the casting sock 119 is provided as a roll, after activation, the tape is unrolled and wrapped around the other components to attach them together to form an upper portion 132 of the prosthetic leg. The water activated settable material may cure within minutes once activated which hardens the casting sock 119. The water activated settable material may also be considered as a water-curable material. The casting sock 119, for example, is a casting sock manufactured by STS.

Figure 4:
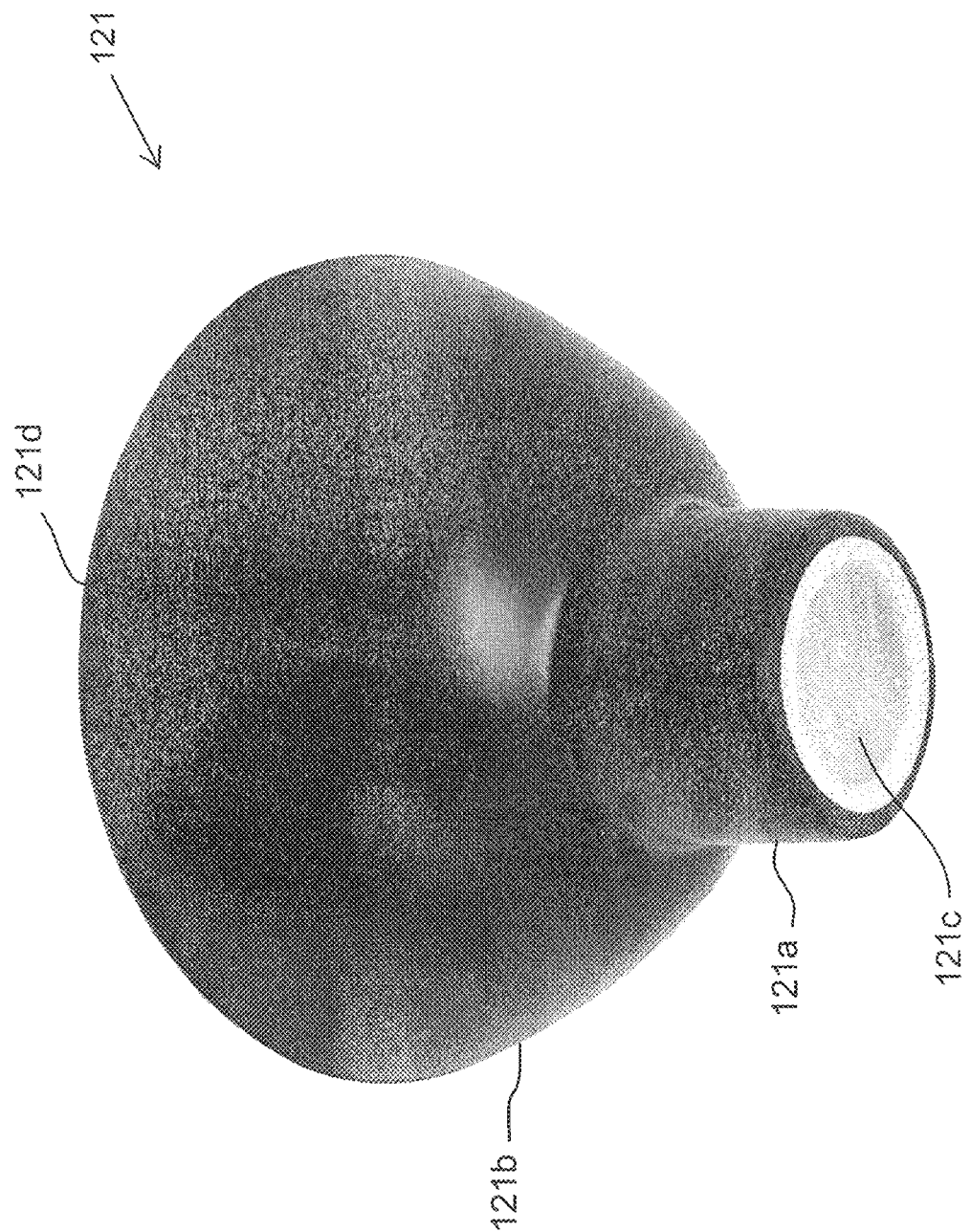
FIGS. 4 and 5 depict illustrative outer coupling members in accordance with some embodiments of the present invention.
Figure 5:
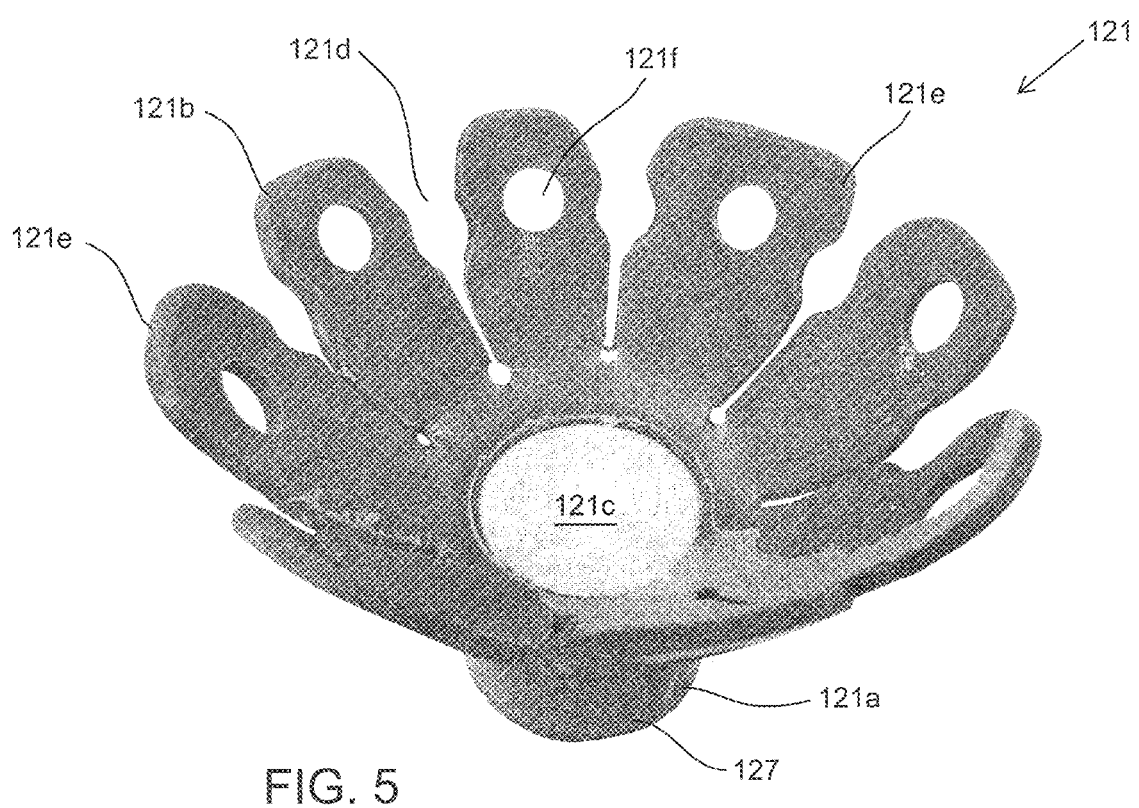

FIGS. 1, 4, and 5 depicts illustrative outer coupling members 115. The outer coupling member 115 has a form as shown in FIG. 4 or FIG. 5. In either form, the outer coupling member 115 has a lower surface 121a and an upper surface 121b. The lower surface 121a includes a socket 121c that is configured and dimensioned to receive a dowel 125 or other component that forms the pylon 127. The upper surface 121b forms a concave opening 121d that is configured and dimensioned to receive the person's stump. The socket 121c has a diameter or circumference that is smaller than that of the opening 121d. The outer coupling members 115 generally has an opening 121d with an approximately three-inch diameter and a socket 121c having an approximately 1-⅛inch diameter The outer coupling member 115 is preferably made of a material comprising a nontoxic thermosetting material or nontoxic heat shrinkable material such as polyvinyl chloride (PVC), polypropylene, polyethylene, terephthalates, polymethacrylate, polycarbonate, polystyrene, or the like. Thus, the outer coupling member 115 is shrinkable at least as to the upper surface 121b so that when heat is applied it can shrink and to conform to and about the inner coupling member 115 and the person's stump. In particular, the upper surface 121b or the opening 121d is at least partially conformable about the concave lower surface 115a of the inner coupling member 115. After heating, the upper surface 121b or the opening 121d engages the other components. In some embodiments, the upper surface 121b or the opening 121d may already fit the person's stump prior to heating in which case heating is not necessary. In this case, however, heating could be applied to further tighten the components. Configurations and dimensions used for the outer coupling member are similar to those described with respect to other components.

The outer coupling member 115 in FIG. 4 is modified to have a structure as shown in FIG. 5. The upper surface 121*b* of the outer coupling member 115 in FIG. 4 is formed with a plurality of petals 121*e* and a hole 121*f* in each of the petals 121*e*. Each petal 121*e* is heated individually and the heated petal 121*e* is adjusted to fit the diverse shape of the person's stump. The person's stump at this point is already protected by the flexible sheath 117, the inner coupling member 115, the distal pad 113, the separator bag 111, and the sock 105 and thus is not in direct physical contact with the heated petals 121*e*. The hole 121*f* is provided to facilitate adjustment since the petal 121*e* may expand in size or deform as it is heated. The kit 100 may include either or both outer coupling members 115.

Referring back to FIG. 1, the casting tape 123 may also comprise a fabric containing a water activated settable material. The fabric is made of fiberglass or another fabric material. The water activated settable material is made with a material similar to the water activated settable material of the casting sock 119. Once activated, the casting tape 123 is applied to wrap at least part of the outer coupling member 121 to the upper portion of the prosthesis that is already formed. The water activated settable material cures within minutes once activated which hardens the casting tape 123. The casting tape 123 provides additional force to hold the outer coupling member 121 and the other components together. The casting tape 123 may come in different width such as two inch, four inch, etc. The casting tape 123, for example, is a premium casting tape manufactured by Techform.

The dowel 125 and the pylon 127 each has a length that is adjustable to provide an overall length for the prosthetic leg to conform the length needed for the person receiving the prosthetic leg. The dowel 125 and the pylon 127 each may come with a length that is longer the missing portion of the leg (or be supplied at the longest length that would be reasonable expected to be used) and is reduced to conform the length needed for the person (or to the same length as the person in need's healthy leg). The dowel 125 and the pylon 127 has the same or different length before or after they are adjusted. The dowel 125 is made of wood or plastic and the pylon 127 is made of plastic. The pylon 127 may comprise a plastic pipe such as a PVC sprinkler or electrical conduit pipe which is readily available. Examples of such a pipe may include, but not limited to, Silver Line PVC 1120 and PVC schedule 40 pipe. The pylon 127 and the dowel 125 has the same or different cross-sectional shape. The pylon 127 typically comprises a hollow plastic tube configured to snugly receive dowel 125 therein. The dowel 125 gives strength and rigidity to the pylon 127 to prevent the pylon 127 from buckling or snapping under the weight of the person once the dowel 125 is inserted into the pylon 127. The dowel 125 is adjusted to be longer than the pylon 127 so that the dowel 125 protrudes from one or both open ends of the pylon 127. The length of the pylon can then be adjusted by a knife, a blade, a saw, or other cutting tool that is readily available to the length needed to properly size the length of the prosthetic leg.

in some embodiments, the kit 100 may comprise two dowels 125 shorter than the pylon 127 so that when each is inserted to each open end of the pylon 127, each dowel 125 or both dowels 125 do not extend through the entire length of the pylon 127. The portion between the dowels 125 in the pylon 127 may remain hollow.

Figure 6:
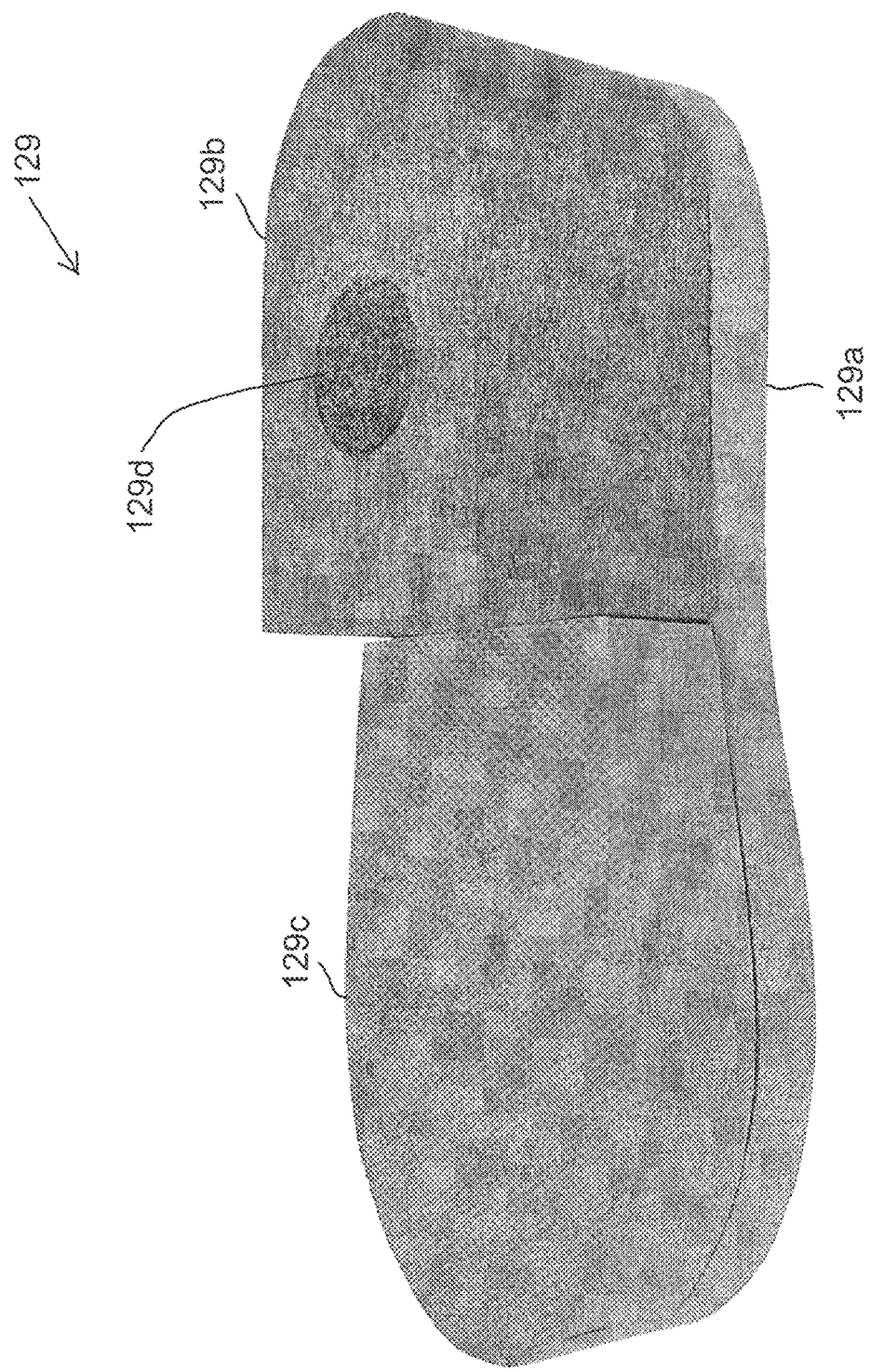
FIG. 6 depicts illustrative components for an artificial foot in accordance with some embodiments of the present invention.

FIG. 6 depicts illustrative components for forming an artificial foot 129. The components may comprise a bottom sole 129*a*, a solid piece of hard material 129*b* (or block 129*b*), and a top sole 129*c*. The block 129*b* and the top sole 129*c* are positioned on the same surface on the bottom sole 129*a*. The block 129*b* may include a hole 129*d* for accommodating the pylon 127 or the dowel 125. The hole 129*d* is located at about two inches from the junction of the block 129*b* and the top sole 129*c*. The components are made of rubber, plastic, wood, or crepe, and are easily adjusted to the appropriate final size and shape by a knife, a blade, a saw, or other cutting tool so that the artificial foot 129 can support the person's weight and is stable to support walking. Preferably, the bottom sole 129*a* is made of rubber, the block 129*b* is made of wood, and the top sole is made of crepe. Adjustment may also be made to the hole 129*d*. The components are referred to as adjustable or shapeable members. The bottom sole 129*a* has a shape resembling a person's foot or a shoe before or after the adjustment. The block 129*b* placed on the bottom sole 129*a* has a height in a direction toward the pylon 127 that is higher than the height of the top sole 129*c* and the bottom sole 129*a* in the same direction. The same height of the top sole 129*c* is also higher than the same height of the bottom sole 120*c* to provide stability and prevent warping or deformation of the bottom sole 129*a*. The top sole 129*a* may also have a weight that is heavier than the weight of the corresponding portion of the bottom sole 129*a* under the top sole 129*a* to gain the same benefits. The top sole 129*c* is adjusted or shaped to cover the remaining area of the surface that is not covered by the block 129*b*. These components are attached together by adhesive 131 to create an artificial foot. The artificial foot can be configured to serve as either a right foot or a left foot thus providing versatility to the kit for use to provide either a right or left prosthetic leg. The components are supplied with one size or the artificial foot is built with one size that typically fits most persons. The artificial foot is described as a SACH foot (solid ankle cushions heel) or Johnson foot.

Referring back to FIG. 1, adhesive 131 may comprise any suitable material such as Neoprene, natural rubber, synthetic rubber, epoxy resin, polyurethane, polyacrylate, polysulfide, cement, and the like. Adhesive is applied to attach any of the components together. Preferably, adhesive 131 is applied to attach the outer coupling member 121 and the pylon 127 or the dowel 125, the artificial foot and the pylon 127 or the dowel 125, the outer coupling member 121 and the person's stump, the distal pad 113 and the inner coupling member 115, and the components for forming the artificial foot 129. Adhesive 131 may comprise multiple packages with each package containing a certain material suitable for attaching specific components together.

The kit 100 may further comprise one or more fork-straps for assisting in retaining the prosthetic leg upon the person's stump during use. The one or more fork-straps are preferably made of leather. The kit 100 may further comprise a cutting tool and a sander to adjust or shape the components in the kit 100. The kit 100 may further comprise one or more screws for securing the components in the kit 100 together. The kit 100 may further comprise other tools necessary for assembling the components in the kit 100. The components in the kit 100 may also come with a configuration and dimension such that they are assembled without any adjustment.

FIG. 7 depicts an illustrative flow chart for the method 700 preparing a prosthetic leg from the prosthetic kit. The entire process is performed quickly with approximately 55 minutes from start to finish. The entire process may also is performed completely on the site of the person in need without having the person in need traveling to a medical office and without sending any mold, part, or component of the prosthetic leg prepared during the process to a manufacturing site or a doctor's office. The components of the kit 100 are assembled by tools readily available such as tools that are sold in a hardware store or convenience store and that can be purchased without substantially delaying the preparation process (e.g., tools that are purchased or otherwise obtained on the spot without special ordering or delivery). The method 700 may commence with pulling the sock 105 over the person's stump (step 705). The separator bag 111 is then pulled over the sock 105 (step 710) to prevent the water activated settable material and water from soaking the sock 105. A portion of the distal pad 113 is placed in the inner coupling member 115 (step 715), especially with the concave lower surface of the distal pad 113 placed in or in contact with the upper inner surface 111*b* of the inner coupling member 115. The flexible sheath 720 is applied to hold the distal pad 113 and the inner coupling member 115 against the person's stump with upper inner surface of the distal pad 113 contacting the person's stump and the concave lower surface of the inner coupling member 115 contacting the closed end of the flexible sheath 720. The open end of the flexible sheath 720 may extend over the separator bag 111 and the sock 105 to hold those components against the person's stump.

The casting sock 119 is then dipped in water, preferably warm water, to activate its water activated settable material. In some embodiments, the casting sock 119 is dipped in water prior to step 705, 710, 715, or 720 while other steps are simultaneously performed. After activation, the casting sock 119 is applied to fit over the flexible sheath 117, the inner coupling member 115, the distal pad 113, and at least of the separator bag and the sock 105 (step 725). The casting sock 119 is applied in a manner to ensure that non-air bubbles or voids are present between the casting sock 119 and the flexible sheath 117.

After the casting sock 119 cures, the outer coupling member 121 is provided to the casting sock 119 on the person's stump (step 730). In some embodiments, the cured casting sock 119 is removed from the person's stump and the subsequent components is applied on the removed casting sock 119. The upper inner surface 121*a* of the outer coupling member 121 is provided beneath the cured casting sock 119. Adhesive 131 is provided between the cured casting sock 119 and the upper inner surface 121*a*. The upper inner surface 121*a* or petals 121*e* are then heated to conform at least partially with the cured casting sock 119. The cured casting sock 119 or the cured casting sock 119 containing all the components applied before the cured casting sock 119 is referred to as a socket which forms the upper portion 132 of the prosthetic leg.

The casting tape 123 is then dipped in water, preferably warm water, to activate its water activated settable material. In some embodiments, the casting tape 123 is dipped in water prior to step 705, 710, 715, 720, 725, or 730 while other steps are simultaneously performed. After activation, the casting sock 119 is wrapped around at least part of the outer coupling member 121 and at least part of the socket to provide additional force bonding the two components. The casting tape 123 is applied in a manner to ensure that non air bubbles or voids are present between the casting tape 123 and the socket and between the casting tape 123 and the outer coupling member 121. The casting tape 123 is wrapped in a manner that has fewer wrinkles. Preferably, the casting tape 123 is wrapped in a "figure eight" manner. (Step. 735.)

Components for forming the artificial foot 129 are adjusted or shaped to provide support and provide stability to the person in need (step. 740). The adjusted or shaped components are joined together by adhesive 131 to create the artificial foot 129. The artificial foot 129 is coated with a waterproof material or a protective material to prolong the life of the artificial foot 129.

The pylon 127 and/or the dowel 125 are cut to the proper length for the person in need (step 745). The proper length may refer to the length of the person in need's healthy leg or the length of the missing portion, After cutting, the dowel 125 is inserted into the pylon 127. After inserting, one end of the pylon 127 and/or the dowel 125 is inserted into and attached to the outer coupling member 121 using adhesive 131 and another end of the pylon 127 and/or the dowel 125 is inserted into and attached to the hole 129*d* of the artificial foot 129 using adhesive 131. A screw is used to screw the dowel 127 inside the pylon 125 to the artificial foot 129. Moreover, a fork-strap is attached to the socket and is used for attaching the prosthetic leg to the person in need by buckling to the remaining limb or the person in need's body.

The person preparing the prosthesis may examine the fit, motion, and dimensions of the prosthetic leg for suitability to the person in need. As the person walks using the prosthetic, the preparing person may watch and examine the operation of the prosthetic on the person in need and make any minor adjustments to the prosthetic.

Figure 8A:
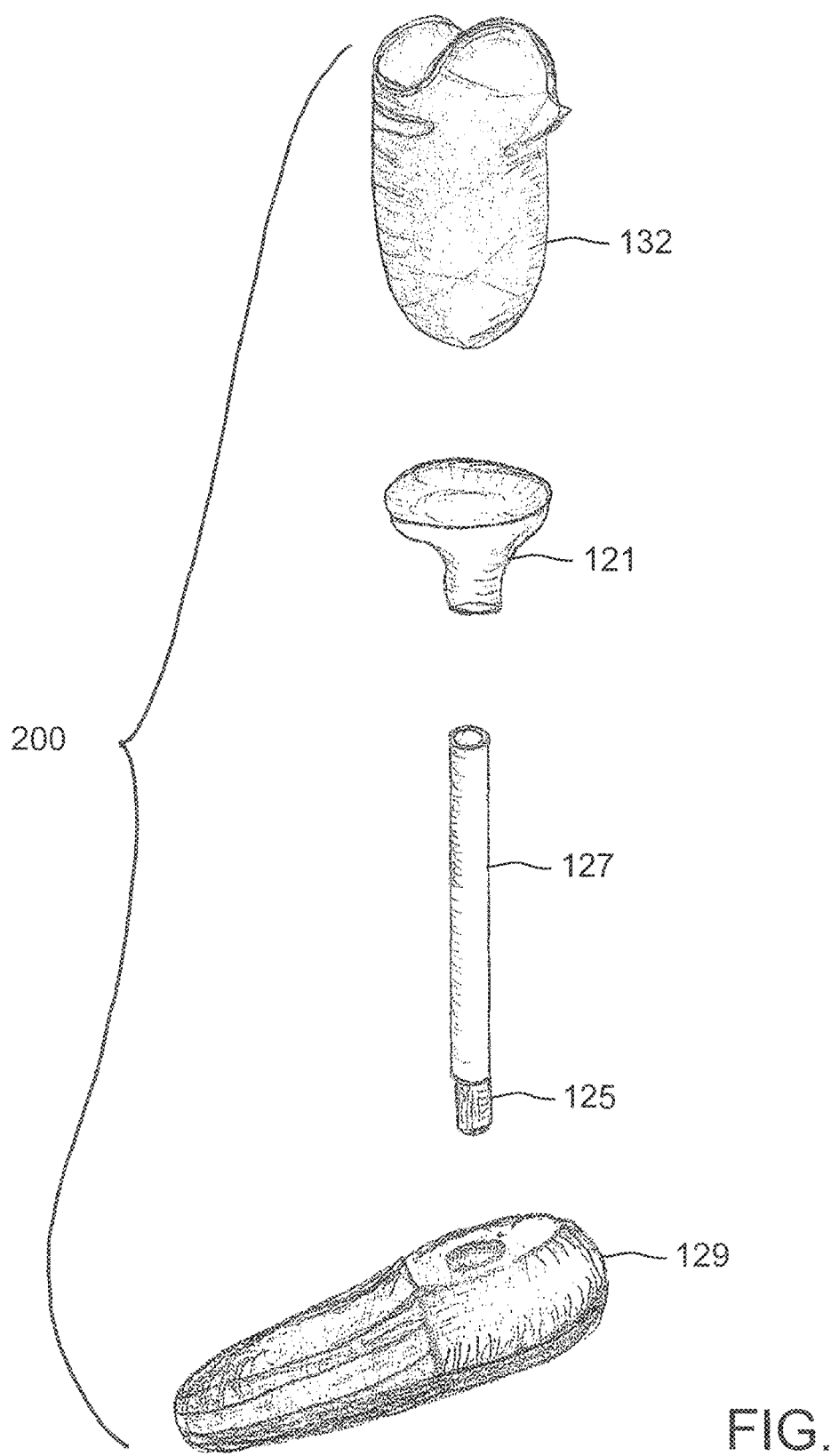
FIGS. 8A and 8B depict a prosthetic leg prepared from the kit of FIG. 1, with FIG. 8A being an exploded view and FIG. 8B being an assembled view of the prosthetic leg.
Figure 8B:
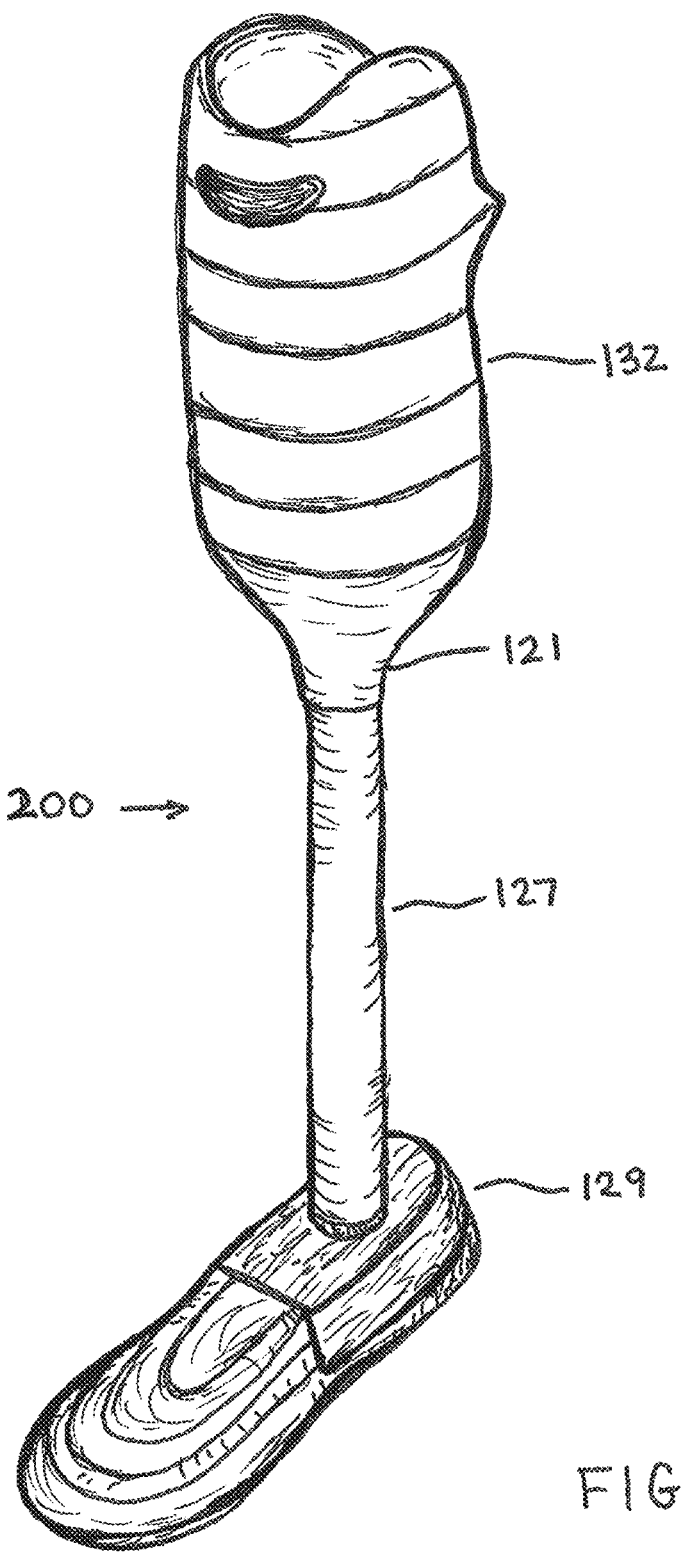

FIGS. 8A and 8B depict the prosthetic leg 200 prepared from the kit 100, with FIG. 8A being an exploded view and FIG. 8B being an assembled view. The prosthetic leg 200 may comprise socket 132 (which may comprise the cured casting sock or the cured casting sock containing all the components applied before the cured casting sock), outer coupling member 121, pylon 127, and artificial foot 129. The remaining components not shown in this figure are covered by one or more of these components.

The prostheses of the present invention can be used to replace a portion of the person's leg below the knee in which case the pylon is sized accordingly and the socket is attached to the persons stump. When the person has lost his or her leg above the knee, the pylon of the prosthesis can be provided in a longer length.

Figure 9:
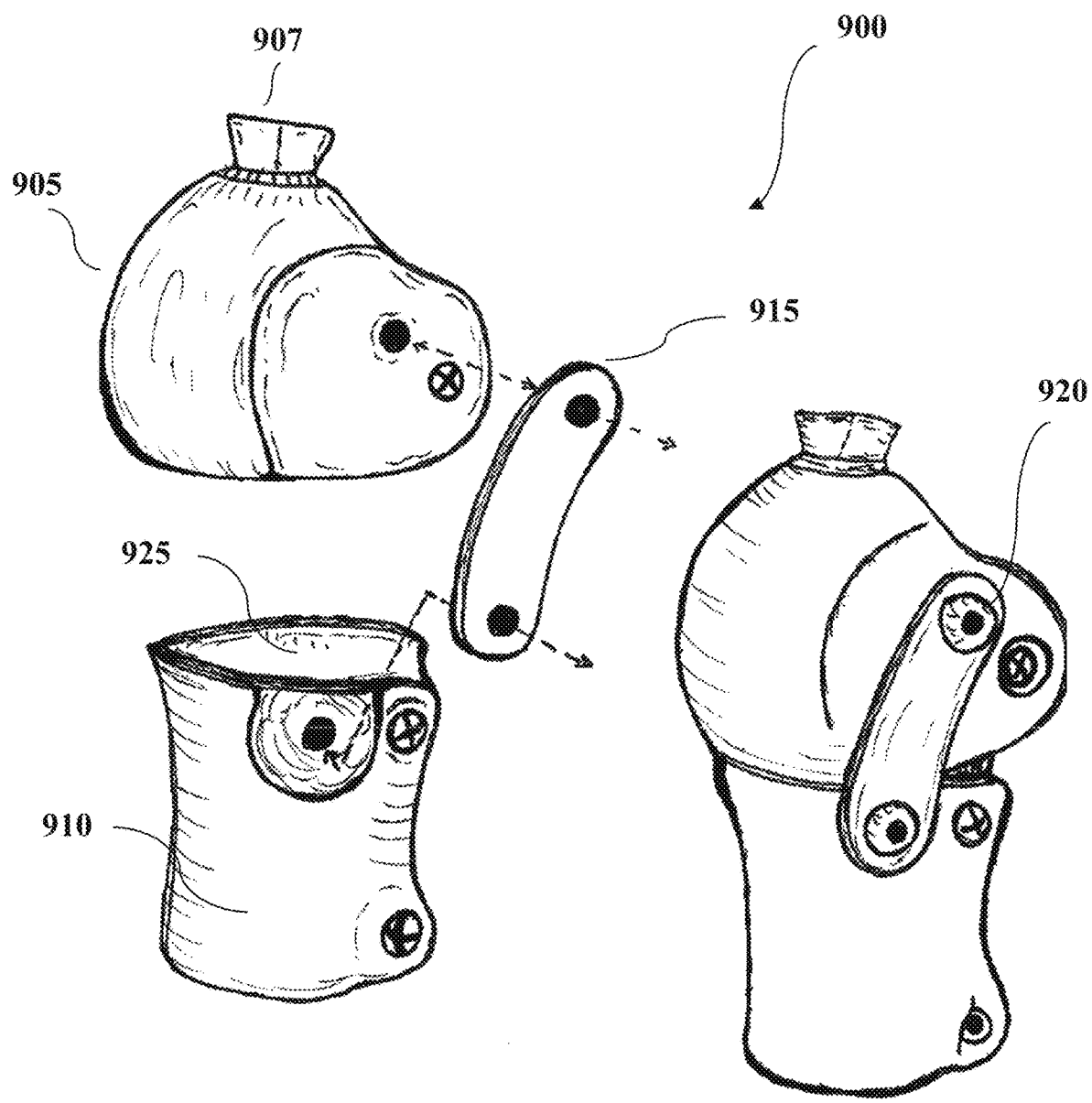
FIG. 9 depicts a commercially available artificial knee for use in the present invention.
Figure 10:
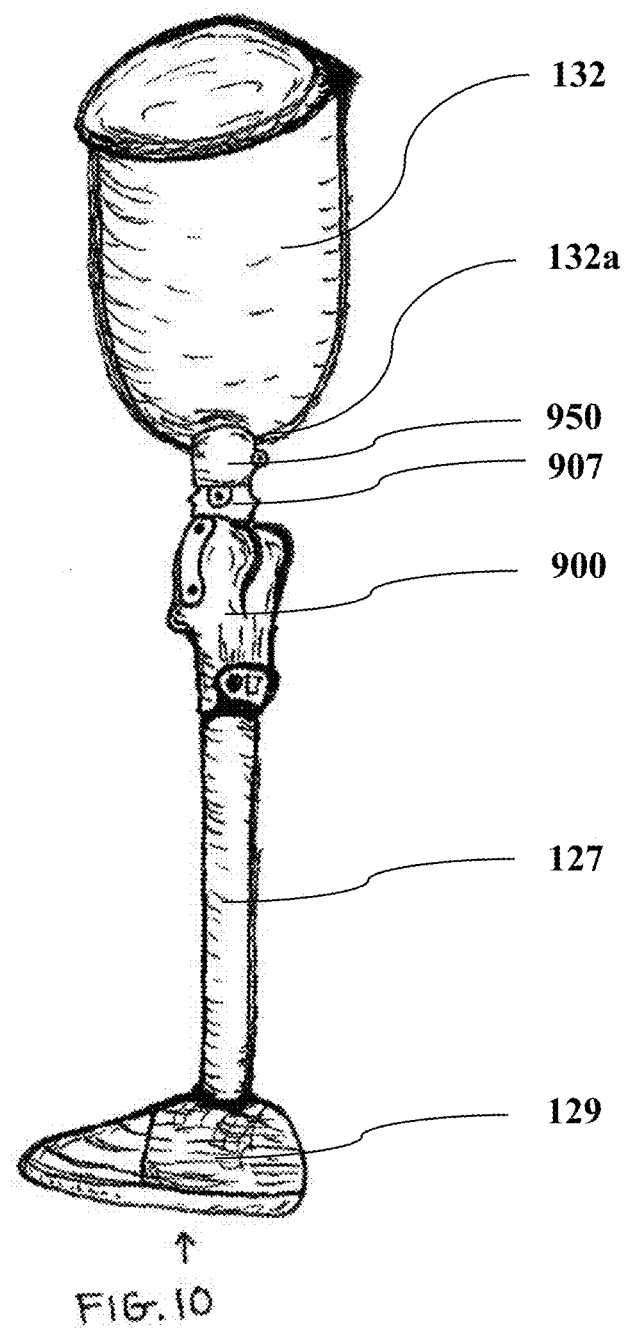
FIG. 10 illustrates a prosthesis for an artificial leg that includes the artificial knee of FIG. 9.

Persons who have lost a leg above the knee have also lost the articulation ability of the knee joint. Thus, in another embodiment of the invention, an articulating knee joint 900 as shown in FIGS. 9 and 10 is provided. This joint 900 is a commercially available low cost artificial knee that is known as the ReMotion Knee Joint (v3) which is available from D-Rev: Design Revolution, 695 Minnesota Street, San Francisco, Calif. 94107 (http://d-rev.org/projects/mobility/). The joint 900 includes an upper portion 905 having a protrusion 907, a lower portion 910, and a plate 920 connecting the upper portion 905 and the lower portion 910 in a manner such that the upper portion 905 is movable with respect to the lower portion 910 (or vice versa). For example, when force is exerted on the upper portion 905 or the protrusion 907, the upper portion 905 is rotated in a direction with the protrusion 907 moving toward the lower portion 910. When force is released, the upper portion 905 is rotated in another direction with the protrusion 907 moving away from the lower portion 910. The upper portion 905 and the lower portion 910 may be in physical contact without interfering their movement. The lower portion 910 includes an opening 925 on which the upper portion 905 is placed. The protrusion 907 may be a pyramid or a pyramid receiver. The plate 920 is connected to the upper portion 905 with a fastener (e.g., screw) and to the lower portion 910 with another fastener. The protrusion 907 includes a structure configured to fit or receive the coupling member or other type of connector 950. The structure and size of the protrusion 907 can be modified to fit or receive the coupling member or other type of connector 950. The other type of connector 950 may be a socket attachment plate with pyramid (or pyramid receiver) and through hole, a multi-prong adapter with pyramid (or pyramid receiver), a rotatable pyramid (or pyramid receiver), and the like.

The joint 900 is connected to the socket 132 from the tip 132a of the socket 132 and is situated in a location corresponding to the person's knee. The joint 900 is connected to the tip 132a via the coupling member or other types of connector 950. The distance between the tip 132a and the joint 900 can be adjusted by changing the length or structure of the protrusion 907, the coupling member, other type of connector 950, or a combination thereof so the location of the joint 900 can be customized for each individual. The pylon 127 is appropriately reduced in size and is connected to the joint 900 via the opening 925 of the lower portion 910. Another end of the pylon 127 is inserted into the artificial foot 129. The joint 900 and the connection discussed enable the person to utilize the prosthesis in the same manner as a normal knee which facilitates movement, motion and sitting. While this does add some cost to the replacement prosthesis, the advantage of having articulating knee movement provides a substantial benefit to the person in providing the ability to move as they did before loss of the leg and knee. Even so, the kit with the artificial knee generally costs less than $100, and the prosthetic leg and knee prepared from the kit by a health care professional would cost than less $300.

FIGS. 9 and 10 depict an illustrative artificial knee that can be used with the prosthetic leg. Other types of artificial knee may also be used with the prosthetic leg. Other types of artificial knee may be connected to the prosthetic leg via the same coupling member or connector used above or a different coupling member or connector configured to fit or receive that particular type of artificial knee.

Figure 11:
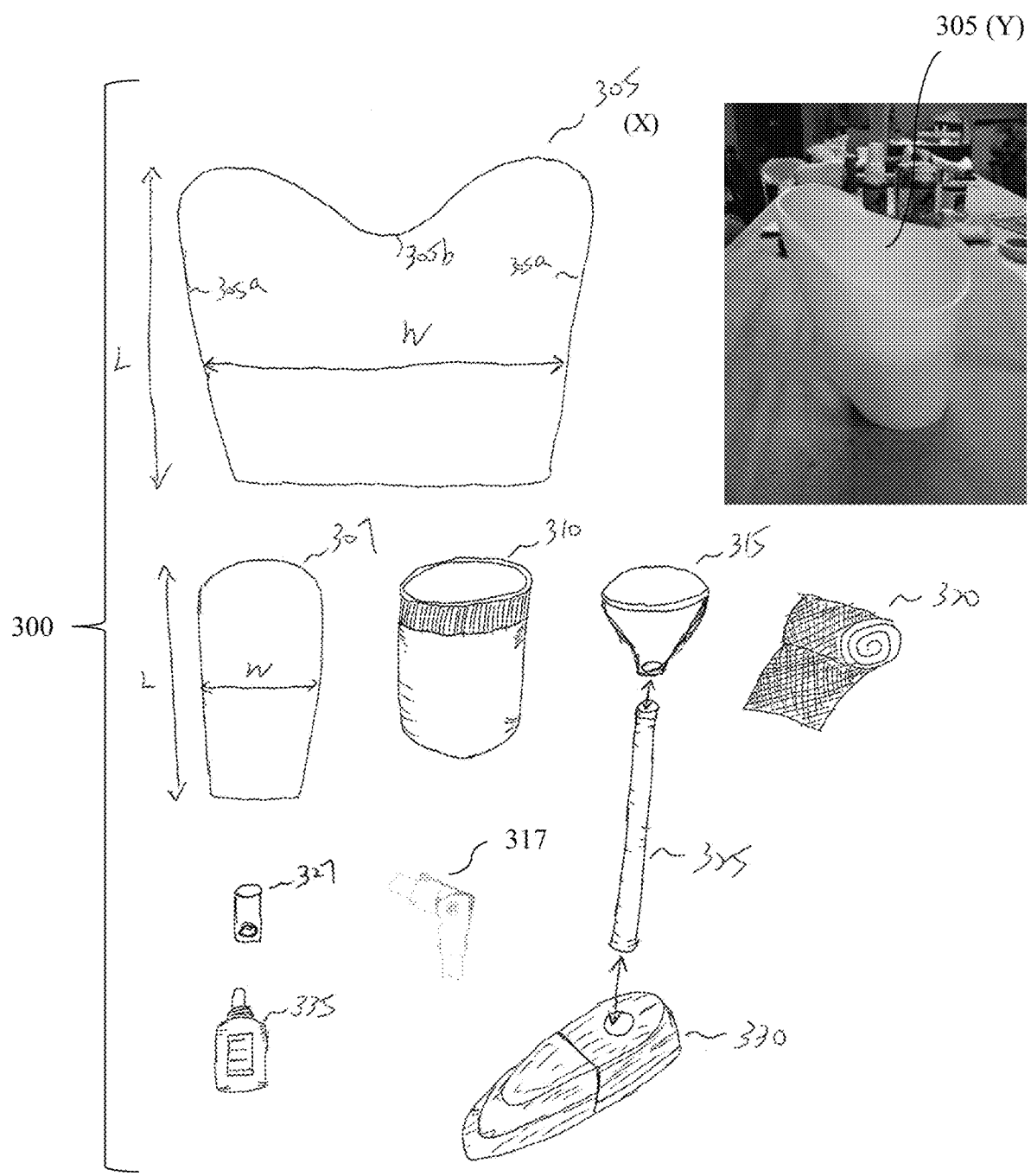
FIG. 11 depicts the components of another prosthetic leg kit according to the present invention.

FIG. 11 depicts another illustrative kit 300 for preparing a prosthetic leg. The kit 300 comprises a plurality of components, including a flexible sheath 305, a casting sock 310, a coupler 315 (or coupling member 315), a casting tape 320, a pylon 325, and an artificial foot 330 (or components for creating an artificial foot 330). The flexible sheath 305 is adapted to fit on and conform to a person's thigh. The flexible sheath 305 covers the thigh circumferentially. The flexible sheath 305 has a width (W) to completely cover the outline or contour of an average person's thigh. The ends or sides 305a of the flexible sheath 305 may contact each other or overlap when the flexible sheath 305 is put on the thigh. The flexible sheath 305 has a circumference, perimeter, or width between approximately 11 inches and approximately 26 inches.

The flexible sheath 305 (Y version of 305) may be made from a flat plastic sheet (X version of 305) that has been warped to generally conform to a person's thigh. The flat plastic sheet has been warped by directing, bending, curving two opposite sides (e.g., vertical sides) of the sheet toward each other. The flat plastic sheet can be warped by heat, pressure, chemical, or a combination thereof, and the resulting flexible sheath 305 is a warped plastic sheet. The warped plastic sheet 305 has a resemblance or shape similar to the character "C" or "O." The warped plastic sheet may have a gap between the two opposite sides and the gap may have a measurement between approximately 0.1 inch and approximately 1 inch. The warped plastic sheet may also have no such gap when the two sides are directed to contact or overlap each other. Gap between 0 and 0.1 inch and larger than 1 inch are also contemplated. The flexible sheath 305 may be a single warped plastic sheet or consist of a single warped plastic sheet.

The flat plastic sheet includes a lower or concave region 305b on the top side to accommodate an inner area of the person's stump (e.g., an area in the groin). The concave region 305b, and/or area adjacent or surrounding the region 305b, may be further configured to have its edge extending away from the flat plastic sheet (or the center of the flexible sheath 305 or from the thigh in warped form).

The flexible sheath 305 (or the flat plastic sheet) has a length (L) (short enough) to expose the person's stump or knee, or a portion of the person's thigh. The flexible sheath 305 has a length between approximately 6 inches and approximately 10 inches. The flexible sheath 305 (or the flat plastic sheet) has a thickness between approximately 0.01 inches and approximately 0.125 inches, The flexible sheath 305 is flexible enough to be opened (e.g., pushing the two sides 305a away from each other), put on the thigh, and closed (e.g., bringing the two sides 305a closer or together, either by the sheath itself due to its elasticity or by hand). The flexible sheath 305 can be opened and then put directly on the thigh, without putting the person's stump or knee in first like a fabric sock. The flexible sheath 305 can be opened from the two sides 305a, such as by pushing the two sides 305 backward, to create an opening that is wide enough to receive the thigh. When the flexible sheath is opened, the flexible sheath is in a stretched form. After the flexible sheath 305 is put on the thigh or when the force exerting on the two sides 305 is released, the flexible sheath 305 "closes," i.e., returns to its original warped form or a position close to its original warped form. When the two sides 305a come into contact, the amount of overlap by the two sides 305a depend on the size of the person's thigh (referring to the contour of the thigh). The flexible sheath 305 can fit on either the person's left or right thigh.

The flexible sheath 305 can be made of polypropylene or other flexible materials. The materials and/or manufacturing processes used should make the final product flexible to be opened, put on the thigh, and closed as described above. The flexible sheath 305 may be waterproof or made of a waterproof material. Unless otherwise noted, the component "the flexible sheath" refers to the Y version of 305 shown in FIG. 11.

In one embodiment, the flexible sheath 305 or the warped plastic sheet can be formed from a mold that has the required shape (e.g., "C" shape). Polypropylene or other flexible materials can be injected into the mold and then be cured or hardened to create the desired structure.

The casting sock 310, coupler 315, casting tape 320, pylon 325, and artificial foot 330 are similar to the casting sock 119, outer coupler 121, casting tape 123, pylon 127, and artificial foot 129 shown in FIG. 1, and the descriptions of the casting sock 119, outer coupler 121, casting tape 123, pylon 127, and artificial foot 129 above also apply to the casting sock 310, coupler 315, casting tape 320, pylon 325, and artificial foot 330. The outer coupler 121 may be other types of couplers as long as it can be used to join the socket (described below) and the pylon 325 together.

The kit 300 may further include a flexible panel 307, an artificial knee 317, an additional pylon 327, and adhesive 335, but these components may be optional. The flexible panel 307 is contoured (or is flexible enough to be contoured) to fit on an arc of the person's thigh. The flexible panel 307 has a width smaller than that of the flexible sheath 305. The flexible panel 307 has a length and thickness similar to those of the flexible sheath 305. The flexible panel 307 can be made of the same materials as the flexible sheath 305 or other materials. The flexible panel 307 can be used when the person has a large thigh and the flexible sheath 305 cannot completely cover the thigh. The flexible panel 307 can be placed on the area that is not covered by the flexible sheath 305 so that the entire contour of the thigh can be covered by the flexible sheath 305 and the flexible panel 307. The width of the flexible panel 307 is sufficient to cover the area that cannot be covered by the flexible sheath 305. The artificial knee 317 may be the knee shown in FIG. 9 or other types of knees. The pylon 327 may be shorter than the pylon 325 and may be used to connect the coupler 315 and the artificial knee 317. Adhesive 335 is similar to adhesive 131 shown in FIG. 1, and the description of adhesive 131 above also applies to adhesive 335. The kit 300 may also include screws, nails, bolts, nuts, washers, screwdrivers, hex keys, wrenches, and other securing mechanisms and tools to help tighten and untighten one or more components if necessary.

The flexible sheath 305, casting sock 310, coupler 315, casting tape 320, pylon 325, and artificial foot 330 may be referred to as the base components. The kit 300 may include the base components. The kit 300 may include the base components and one or more of the aforementioned optional components. The kit 300 may consist of the base components. The kit 300 may consist of the base components and one or more of the aforementioned optional components. Other combinations are also contemplated.

A method of preparing a prosthetic leg from the kit 300 is described in FIG. 7. The method commences by applying the flexible sheath 305 to the person's stump or thigh (starts with step 720, instead of step 705 for kit 100). If necessary, the flexible panel 307 may also be used. After applying the flexible sheath 305 (and the flexible panel 307 if necessary), part of the person's stump is exposed (e.g., tip or front end of the stump). The casting sock 310 is dipped in water, preferably warm water, to activate its water activated settable material. The casting sock 310 can be dipped in water prior, during, or after step 720. After activation, the casting sock 310 is applied to fit over the flexible sheath 305 (and the flexible panel 307 if it is used) from the exposed stump (step 725).

After the casting sock 310 cures, a socket is formed, similar to socket 132 shown in FIGS. 1, 8, and 10. Since the socket is created on the stump, the stump is already in the socket when the socket is created. The coupler 315 is provided to the tip of the socket (step 730). The casting tape 320 is dipped in water, preferably warm water, to activate its water activated settable material. The casting tape 320 can be dipped in water prior, during, or after step 720, 725, or 730. After activation, the casting sock 310 is wrapped around at least part of the coupler 315 and at least part of the socket to bond the two components (step 735). The casting tape 320 is applied in a manner to ensure that no air bubbles or voids are present between the casting tape 320 and the socket and between the casting tape 320 and the coupler 315. The casting tape 320 is wrapped in a manner that has fewer wrinkles. Preferably, the casting tape 320 is wrapped in a "figure eight" manner. In some embodiments, the socket may refer to the structure after the casting tape 320 is applied.

The artificial foot 330 and the pylon 325 can be utilized (or created) and attached to the socket in manners discussed in step 740 and 745 for the kit 100 and will not be repeated for the sake of brevity. Step 740 and 750, whether they are steps for the kit 100 or 300, can be performed prior, during, or after step 720, 725, 730, or 735.

The additional pylon 327 and the artificial knee 317 can also be utilized. For example, the additional pylon 327 can be used to connect the coupler 315 and the artificial knee 317 together. The coupler 315 and the artificial knee 317 each includes a structure for receiving each end of the pylon 327. The additional pylon 327 may be provided after step 735. The artificial knee 317 can be installed after the additional pylon 327 is connected to the coupler 315.

Figure 12:
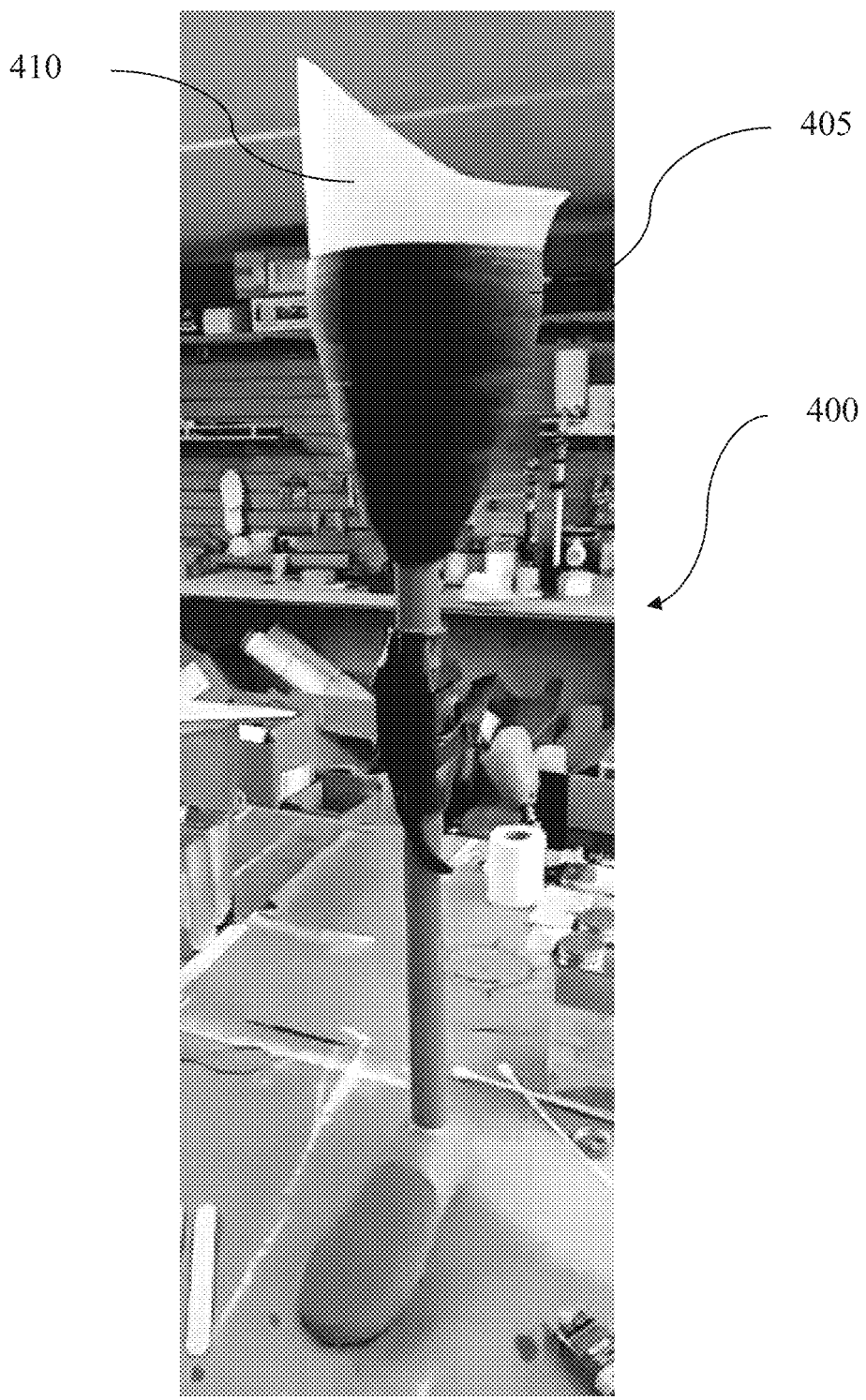
FIG. 12 depicts an illustrative prosthetic leg prepared from the components shown in FIG. 11.
Figure 13:
FIG. 13 depicts a perspective view of the flexible sheath with the flexible panel in accordance with some embodiments of the present invention.
Figure 14:
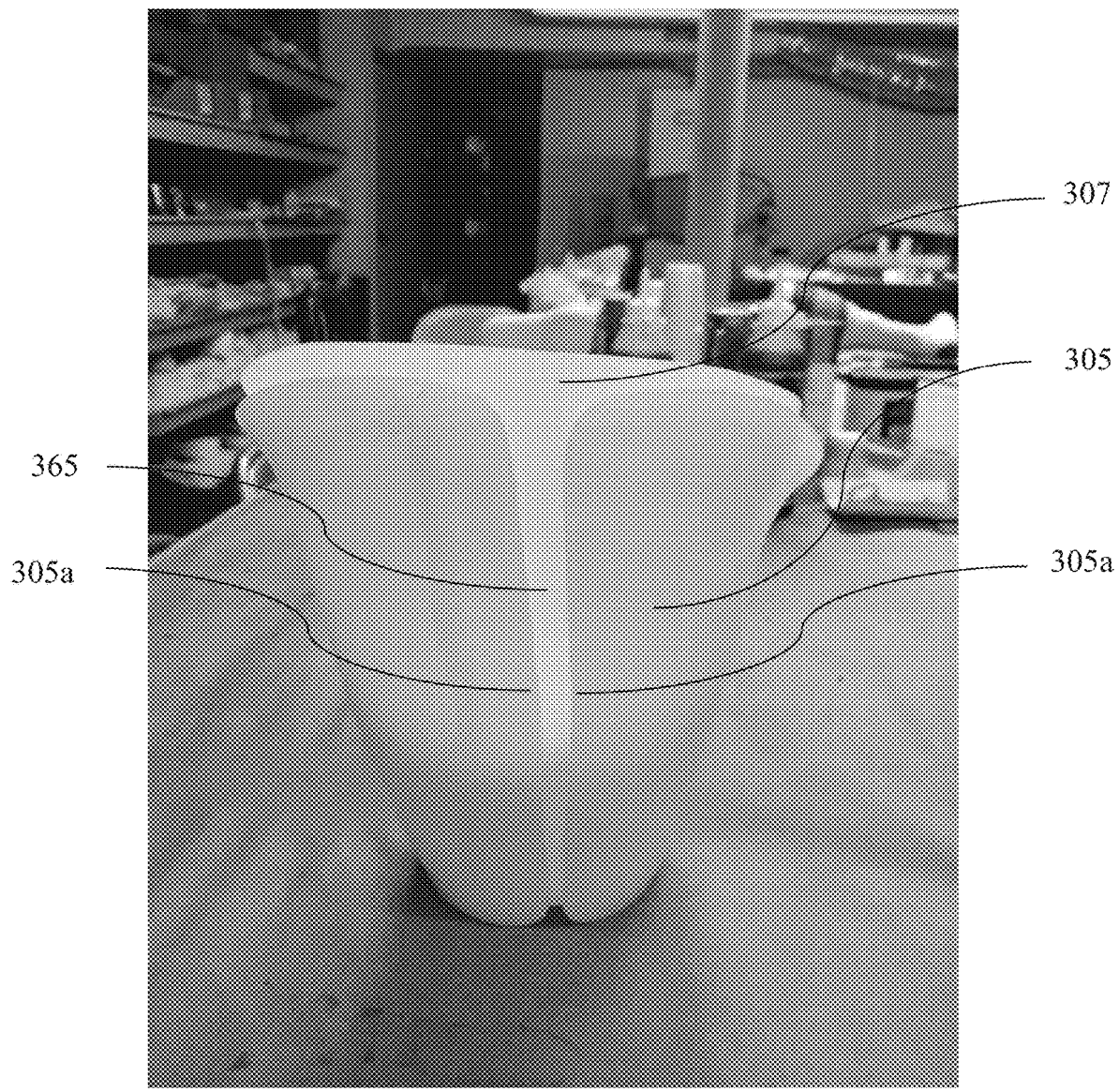
FIG. 14 depicts a rear view or bottom view of the flexible sheath with the flexible panel in accordance with some embodiments of the present invention.
Figure 15:
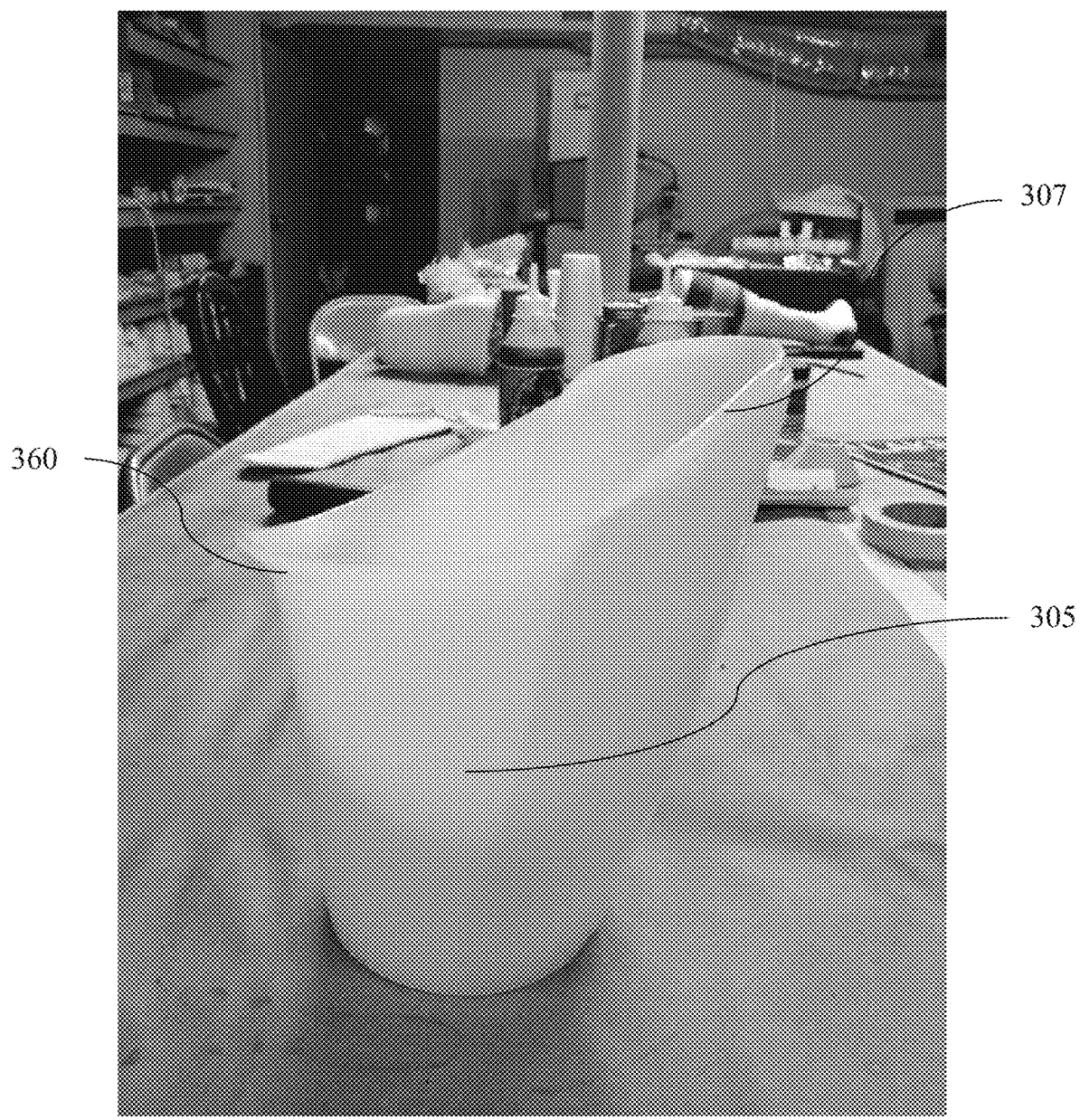
FIG. 15 depicts another perspective view of the flexible sheath with the flexible panel in accordance with some embodiments of the present invention.

Since the preparation method using the kit 300 involves a fewer number of steps (steps 705-715 are not performed), the entire process may be shorter than the entire process using the kit 100. This method may only require about 35 minutes. FIG. 12 depicts an illustrative prosthetic leg 400 prepared from the kit 300. The prosthetic leg 400 includes the additional pylon and the artificial knee, and it is understood that those components may be optional. The artificial knee 317 may also be directly connected to the coupler 315 without using the additional pylon 327 if the artificial knee 317 and the coupler 315 are configured to engage each other. The prosthetic leg 400 also shows the socket 405 created using components from the kit 300. The portion not wrapped by the casting tape may be referred to as the rim 410. The rim 410 is flexible and adjustable to fit on either the person's right or left stump.

Figure 16:
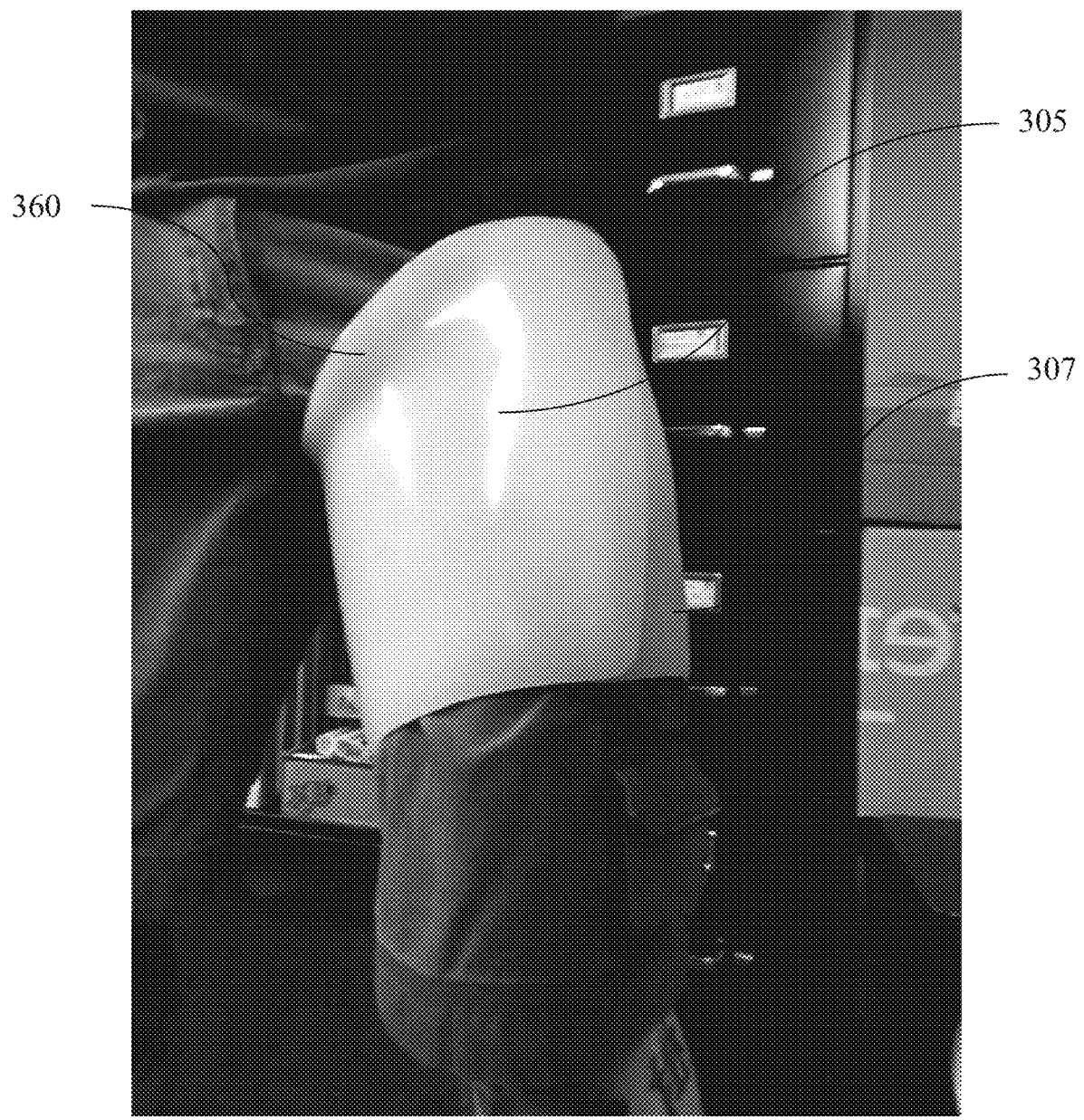
FIG. 16 depicts application of the flexible sheath and the flexible panel on a person's thigh in accordance with some embodiments of the present invention.
Figure 17:
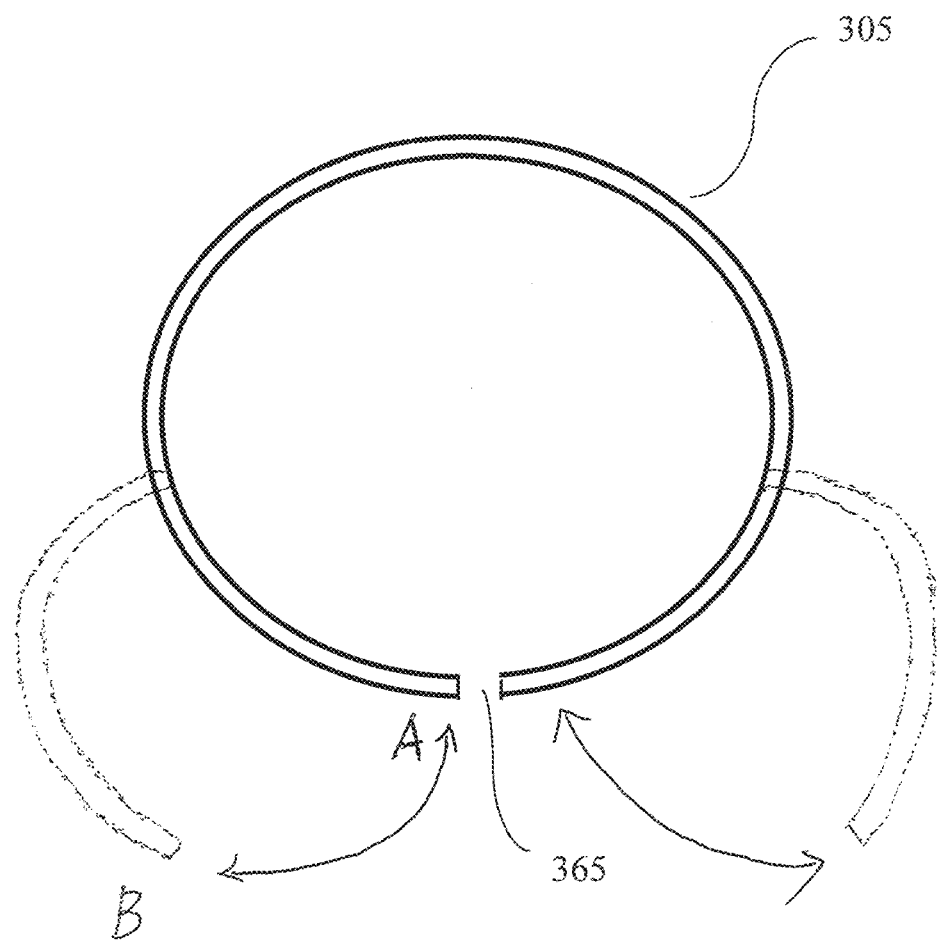
FIG. 17 is an illustrative top view of the flexible sheath showing that the flexible sheath is flexible enough to be opened and closed by hands, or to be opened by hands and close on its own due to its elasticity.
Figure 18:
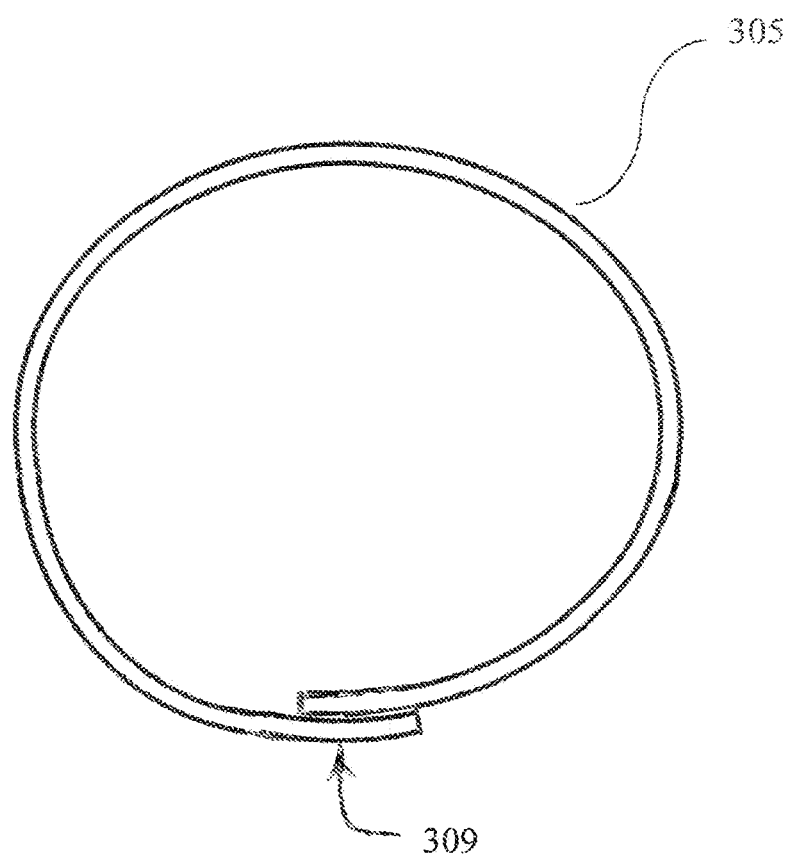
FIG. 18 is an illustrative top view of the flexible sheets showing that the flexible sheet is flexible enough to be closed with overlapping ends for certain embodiments.

FIGS. 13-18 are views of the flexible sheath 305 with the flexible panel 307 in accordance with some embodiments of the present invention. Views or structures of the flexible sheath alone (without the flexible panel 307) are also understood from these figures. FIGS. 13-16 also show the edge 360 of the top side of the flexible sheath 305 extending away from the center of the flexible sheet 305 and the gap 365 between the two opposite side 305a of the flexible sheet 305. Although FIG. 16 shows the flexible sheath 305 and the flexible panel 307 applied over the person's shorts, an actual application the flexible sheath 305 and the flexible panel 307 are applied on the person's stump or thigh. FIG. 17 is an illustrative cross-sectional, side view, or top view of the flexible sheath 305 showing that the flexible sheath 305 is flexible enough to be opened (position B) and closed (position A) by hands, or to be open (position B) by hands and closed (position A) on its own due to its elasticity. FIG. 18 is an illustrative cross-sectional, side view, or top view of the flexible sheath 305 showing that the ends of the flexible sheath can overlap at 309 in a more fully closed position when the flexible sheath 305 is placed on a person's stump or thigh of smaller size than the circumferential width of the flexible sheath 305.

As used herein, the term "the person's stump" may refer to the person's stump prior to any component is applied or after one or more components are applied to the person's stump. For example, the person's stump may refer to the person's stump covered by one or more of the sock, the separator bag, the distal pad, inner couple member, the flexible sheath, and/or the casting sock, depending on the progress of the method.

Reference to a particular physical dimension (such as length, width, and thickness) or time (e.g., 55 minutes and 35 minutes) is understood to refer to that specific number and to a range at or about ±25% of the number unless a specific percentage is specified for that dimension or time.

Although embodiments of the present invention illustrate a prosthetic in the form of a leg, they can be provided for a different body part such as an arm or other missing body parts for which a prosthetic is suitable. Many of the same materials and process steps are followed with of course appropriate adjustment for provided, e.g., a hand instead of a foot component, a ratcheted component for an elbow in the pylon, etc. Skilled artisans can understand how to adapt the invention disclosed herein for replacement of an arm instead of a leg and for that reason those embodiments are also contemplated by the present invention.

In the foregoing specification, the invention has been described with reference to specific embodiments thereof. It will, however, be evident that various modifications and changes is made thereto without departing from the broader spirit and scope of the invention. For example, the reader is to understand that the specific ordering and combination of process actions shown in the process flow diagrams described herein is merely illustrative, and the invention can be performed using different or additional process actions, or a different combination or ordering of process actions. As another example, each feature of one embodiment can be mixed and matched with other features shown in other embodiments. Features and processes known to those of ordinary skill in the art of identification appliances may similarly be incorporated as desired. Additionally and obviously, features is added or subtracted as desired. Accordingly, the invention is not to be restricted.

What is claimed is:

1. A kit for preparing a prosthetic leg for a person having a missing portion of a leg and a remaining stump, the kit having a plurality of components consisting of:
    a flexible sheath adapted to fit on the person's stump, wherein the flexible sheath consists of a warped plastic sheet having two opposite sides being curved toward each other and configured as an initially restricted opening that is smaller than a person's stump, with the sides being flexible to be moved away from each other to form a stump receiving opening that is configured to receive the person's stump therein to fit the flexible sheath on the person's stump, wherein the moved away sides attempt to return to the configuration of the initially restricted opening due to the elasticity of the warped plastic sheet to self-close and directly secure the sheath on the person's stump;
    a casting sock of a fabric containing a water activated settable material that, after activation, is adapted to fit over the flexible sheath;
    a coupling member having a lower surface that includes an opening, and an upper surface configured to receive the person's stump covered by the casting sock;
    casting tape of a fabric containing a water activated settable material and provided in one or more lengths that, after activation, attach the coupling member to the person's stump while also covering the flexible sheath;
    a first pylon of a wooden dowel within a plastic tube configured to engage the coupling member, wherein the first pylon has a length that is adjustable to provide an overall length for the prosthetic leg to conform to the length needed for the person;
    an artificial foot having a hole for accommodating the first pylon; and
    an adhesive or screws for attaching the pylon or wooden dowel to the hole of the foot component and to the socket opening of the coupling member.

2. The kit of claim 1, wherein the flexible sheath includes a gap of between 0.1 inch and 1 inch between the two opposite sides.

3. The kit of claim 1, wherein the warped plastic sheet of the flexible sheath has a distal concave region along the sheet width that provides a varying length to the sheet with the lengths of the sides being greater than the length of the concave region.

4. The kit of claim 1, wherein the distal concave region is configured to accommodate the person's stump.

5. The kit of claim 4, wherein the concave region or area surrounding the concave region is configured to have its edge extending away from the warped plastic sheet.

6. The kit of claim 1, wherein the two opposite sides of the flexible sheath contact or overlap each other.

7. The kit of claim 1, wherein the casting tape has fabric or fiberglass reinforcement and the settable material is a polyurethane resin.

8. A kit for preparing a prosthetic leg for a person having a missing portion of a leg and a remaining stump, the kit having a plurality of components consisting of:
    a flexible sheath adapted to fit on the person's stump, wherein the flexible sheath consists of a warped plastic sheet having two opposite sides being curved toward each other and configured as an initially restricted opening that is smaller than a person's stump, with the sides being flexible to be moved away from each other to form a stump receiving opening that is configured to receive the person's stump therein to fit the flexible sheath on the person's stump, wherein the moved away sides attempt to return to the configuration of the initially restricted opening due to the elasticity of the warped plastic sheet to self-close and directly secure the sheath on the person's stump;
    a casting sock of a fabric containing a water activated settable material that, after activation, is adapted to fit over the flexible sheath;
    a coupling member having a lower surface that includes an opening, and an upper surface configured to receive the person's stump covered by the casting sock;
    casting tape of a fabric containing a water activated settable material and provided in one or more lengths that, after activation, attach the coupling member to the person's stump while also covering the flexible sheath;
    a first pylon of a wooden dowel within a plastic tube configured to engage the coupling member, wherein the first pylon has a length that is adjustable to provide an overall length for the prosthetic leg to conform to the length needed for the person; an artificial foot having a hole for accommodating the first pylon;
    and an adhesive or screws for attaching the pylon or wooden dowel to the hole of the foot component and to the socket opening of the coupling member;
    with the kit including a flexible panel configured to fit on an arc of the person's stump.

9. The kit of claim 8, wherein the flexible panel has a width shorter than that of the plastic sheet.

10. A kit for preparing a prosthetic leg for a person having a missing portion of a leg and a remaining stump, the kit having a plurality of components consisting of:
    a flexible sheath adapted to fit on the person's stump, wherein the flexible sheath consists of a warped plastic sheet having two opposite sides being curved toward each other and configured as an initially restricted opening that is smaller than a person's stump, with the sides being flexible to be moved away from each other to form a stump receiving opening that is configured to receive the person's stump therein to fit the flexible sheath on the person's stump, wherein the moved away sides attempt to return to the configuration of the initially restricted opening due to the elasticity of the warped plastic sheet to self-close and directly secure the sheath on the person's stump;

a casting sock of a fabric containing a water activated settable material that, after activation, is adapted to fit over the flexible sheath;

a coupling member having a lower surface that includes an opening, and an upper surface configured to receive the person's stump covered by the casting sock;

casting tape of a fabric containing a water activated settable material and provided in one or more lengths that, after activation, attach the coupling member to the person's stump while also covering the flexible sheath;

a first pylon of a wooden dowel within a plastic tube configured to engage the coupling member, wherein the first pylon has a length that is adjustable to provide an overall length for the prosthetic leg to conform to the length needed for the person;

an artificial knee joint that is operatively associated with the first pylon to provide knee movement to the prosthesis when constructed;

a second pylon of a wooden dowel within a plastic tube, wherein the second pylon is shorter than the first pylon and is configured to connect the artificial knee to the coupling member;

an artificial foot having a hole for accommodating the first pylon; and an adhesive or screws for attaching the first pylon or its wooden dowel to the hole of the foot component and to the artificial knee joint, and for attaching the second first pylon or its wooden dowel to the artificial knee joint and to the opening of the coupling member.

11. A method for preparing a prosthetic leg from a kit of components for a person having a missing portion of a leg and a remaining stump, wherein the kit consists of:

a flexible sheath adapted to fit on the person's stump, wherein the flexible sheath consists of a warped plastic sheet having two opposite sides being curved toward each other and configured as an initially restricted opening that is smaller than a person's stump, with the sides being flexible to be moved away from each other to form a stump receiving opening that is configured to receive the person's stump therein to fit the flexible sheath on the person's stump, wherein the moved away sides attempt to return to the configuration of the initially restricted opening due to the elasticity of the warped plastic sheet to self-close and directly secure the sheath on the person's stump;

a casting sock of a fabric containing a water activated settable material that, after activation, is adapted to fit over the flexible sheath;

a coupling member having a lower surface that includes an opening, and an upper surface configured to receive the person's stump covered by the casting sock;

casting tape of a fabric containing a water activated settable material and provided in one or more lengths that, after activation, attach the coupling member to the person's stump while also covering the flexible sheath;

a first pylon of a wooden dowel within a plastic tube configured to engage the coupling member, wherein the first pylon has a length that is adjustable to provide an overall length for the prosthetic leg to conform to the length needed for the person;

an artificial foot having a hole for accommodating the first pylon; and an adhesive or screws for attaching the pylon or wooden dowel to the hole of the foot component and to the socket opening of the coupling member; and wherein the method comprises:

applying the flexible sheath on the person's stump, wherein the flexible sheath is applied by opening the flexible sheath by pushing the two opposite sides away from each other, placing the opened flexible sheath on the person's stump, and allowing the flexible sheath to attempt to return to the initially restricted opening to close and secure the sheath on the person's stump;

activating the casting sock by immersion in water and applying the activated casting sock to the flexible sheath;

providing the coupling member beneath the casting sock with the upper surface of the coupling member contacting the casting sock;

activating the casting tape by immersion in water;

attaching the coupling member to the person's stump covered by the casting sock by wrapping the activated casting tape around the coupling member while also covering the flexible sheath;

cutting the first pylon to an appropriate length so that the prosthetic leg matches the anatomical leg length of the person; and attaching one end of the first pylon to the opening on the lower surface of the coupling member and the other end of the first pylon to the hole in the artificial foot.

12. The method of claim 11, wherein the flexible sheath is applied on the person's stump to expose a front end of the person's stump.

13. The method of claim 12, wherein the activated casting sock is applied to the flexible sheath from the exposed front end of the person's stump.

14. The method of claim 11, which further comprises applying a flexible panel to fit on an arc of the person's stump, with the flexible panel applied to cover areas not covered by the flexible sheath.

15. The method of claim 11, wherein an artificial knee is provided and the first pylon is cut with a saw or knife to receive the artificial knee and to position the artificial knee at a location that matches that of the anatomical leg of the person.

16. The method of claim 15, which further comprises installing a second pylon, the second pylon comprising a wooden dowel within a plastic tube and the second pylon is installed to connect the artificial knee and the coupling member.

17. The method of claim 11, wherein the casting tape is applied in a manner to ensure that no air bubbles or voids are present between the casting tape and the coupling member and between the casting tape and the casting sock.

18. A method for preparing a prosthetic leg from a kit of components for a person having a missing portion of a leg and a remaining stump, wherein the kit consists of:

a flexible sheath adapted to fit on the person's stump, wherein the flexible sheath consists of a warped plastic sheet having two opposite sides being curved toward each other and configured as an initially restricted opening that is smaller than a person's stump, with the sides being flexible to be moved away from each other to form a stump receiving opening that is configured to receive the person's stump therein to fit the flexible sheath on the person's stump, wherein the moved away sides attempt to return to the configuration of the initially restricted opening due to the elasticity of the warped plastic sheet to self-close and directly secure the sheath on the person's stump;

a casting sock of a fabric containing a water activated settable material that, after activation, is adapted to fit over the flexible sheath;

a coupling member having a lower surface that includes an opening, and an upper surface configured to receive the person's stump covered by the casting sock;

casting tape of a fabric containing a water activated settable material and provided in one or more lengths that, after activation, attach the coupling member to the person's stump while also covering the flexible sheath;

a first pylon of a wooden dowel within a plastic tube configured to engage the coupling member, wherein the first pylon has a length that is adjustable to provide an overall length for the prosthetic leg to conform to the length needed for the person;

an artificial knee joint that is operatively associated with the first pylon to provide knee movement to the prosthesis when constructed;

a second pylon of a wooden dowel within a plastic tube, wherein the second pylon is shorter than the first pylon and is configured to connect the artificial knee to the coupling member;

an artificial foot having a hole for accommodating the first pylon; and an adhesive or screws for attaching the first pylon or its wooden dowel to the hole of the foot component and to the artificial knee joint, and for attaching the second first pylon or its wooden dowel to the artificial knee joint and to the opening of the coupling member; and wherein the method comprises:

applying the flexible sheath on the person's stump, wherein the flexible sheath is applied by opening the flexible sheath by pushing the two opposite sides away from each other, placing the opened flexible sheath on the person's stump, and allowing the flexible sheath to attempt to return to the initially restricted opening to close and secure the sheath on the person's stump;

activating the casting sock by immersion in water and applying the activated casting sock to the flexible sheath;

providing the coupling member beneath the casting sock with the upper surface of the coupling member contacting the casting sock;

activating the casting tape by immersion in water;

attaching the coupling member to the person's stump covered by the casting sock by wrapping the activated casting tape around the coupling member while also covering the flexible sheath;

cutting the first pylon and second pylons to appropriate lengths so that the prosthetic leg and artificial knee matches that of the anatomical leg length and knee position of the person;

attaching one end of the first pylon to the artificial knee and the other end of the first pylon to the hole in the artificial foot; and attaching one end of the second pylon to the opening on the lower surface of the coupling member and the other end of the second pylon to the artificial knee.

* * * * *